United States Patent
Duysens et al.

(12) 
(10) Patent No.: US 6,360,130 B1
(45) Date of Patent: Mar. 19, 2002

(54) TEMPORARY BI-POLAR HEART WIRE

(75) Inventors: Victor P. J. Duysens, Grevenbicht; Paulus C. Van Venrooij, Hoensbroek, both of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/164,066

(22) Filed: Sep. 30, 1998

(51) Int. Cl.[7] .................................. A61N 1/05
(52) U.S. Cl. ........................ 607/132; 607/119
(58) Field of Search .................. 607/119, 122, 607/132

(56) References Cited

U.S. PATENT DOCUMENTS

| | | | |
|---|---|---|---|
| 3,035,583 A | 4/1962 | Hirsch et al. | 128/335.5 |
| 3,125,095 A | 3/1964 | Kaufman et al. | 128/335.5 |
| 3,664,347 A | 5/1972 | Harmjanz | 128/404 |
| 3,949,756 A | 4/1976 | Ace | 128/339 |
| 4,010,756 A | 3/1977 | DuMont et al. | 128/404 |
| 4,054,144 A | 10/1977 | Hoffman et al. | 128/339 |
| 4,338,947 A | 7/1982 | Williams | 128/642 |
| 4,341,226 A | 7/1982 | Peters | 128/784 |
| 4,010,756 C1 | 11/1983 | DuMont et al. | 128/786 |
| 4,442,840 A | 4/1984 | Wojciechowicz, Jr. | 128/419 P |
| 4,444,207 A | 4/1984 | Robicsek | 128/785 |
| 4,530,368 A | 7/1985 | Saulson et al. | 128/784 |
| 4,541,440 A | 9/1985 | Parsonnet | 128/785 |
| 4,553,554 A | 11/1985 | Lemole | 128/784 |
| 4,630,617 A | 12/1986 | Ritter et al. | 128/784 |
| 4,633,880 A | 1/1987 | Osypka et al. | 128/642 |
| 4,693,258 A | 9/1987 | Osypka et al. | 128/783 |
| 4,972,833 A | 11/1990 | Wildon | 128/419 P |
| 5,217,027 A | 6/1993 | Hermens | 128/784 |
| 5,241,957 A | 9/1993 | Camps et al. | 607/119 |
| 5,314,463 A | 5/1994 | Camps et al. | 607/129 |
| 5,350,419 A | 9/1994 | Bendel et al. | 607/132 |
| 5,423,876 A | 6/1995 | Camps et al. | 607/116 |
| 5,792,217 A | 8/1998 | Camps et al. | 607/119 |
| 5,871,528 A * | 2/1999 | Camps et al. | 607/132 |

OTHER PUBLICATIONS

U.S. Patent Appln. Ser. No. 08/818,069 to Camps et al. for "Temporary Bipolar Heart Wire" filed Mar. 14, 1997.*

* cited by examiner

Primary Examiner—Carl H. Layno
(74) Attorney, Agent, or Firm—Thomas F. Woods; Girma Wolde-Michael; Harold R. Patton

(57) ABSTRACT

A low-cost temporary lead for pacing, sensing, monitoring, or defibrillating at least a portion of a human or animal organ, and methods for implanting and making same. The lead has at least two electrodes and distal and proximal ends, and a novel weakened zone disposed between the blunt end of a needle and at least two electrical connectors attached to the proximal end of the lead body. The novel weakened zone permits the needle to be separated from the connectors by application of a sufficiently large bending moment or pulling force thereto. Following separation of the connectors from the needle, the connectors may be attached directly and quickly to an external electrical apparatus.

63 Claims, 20 Drawing Sheets

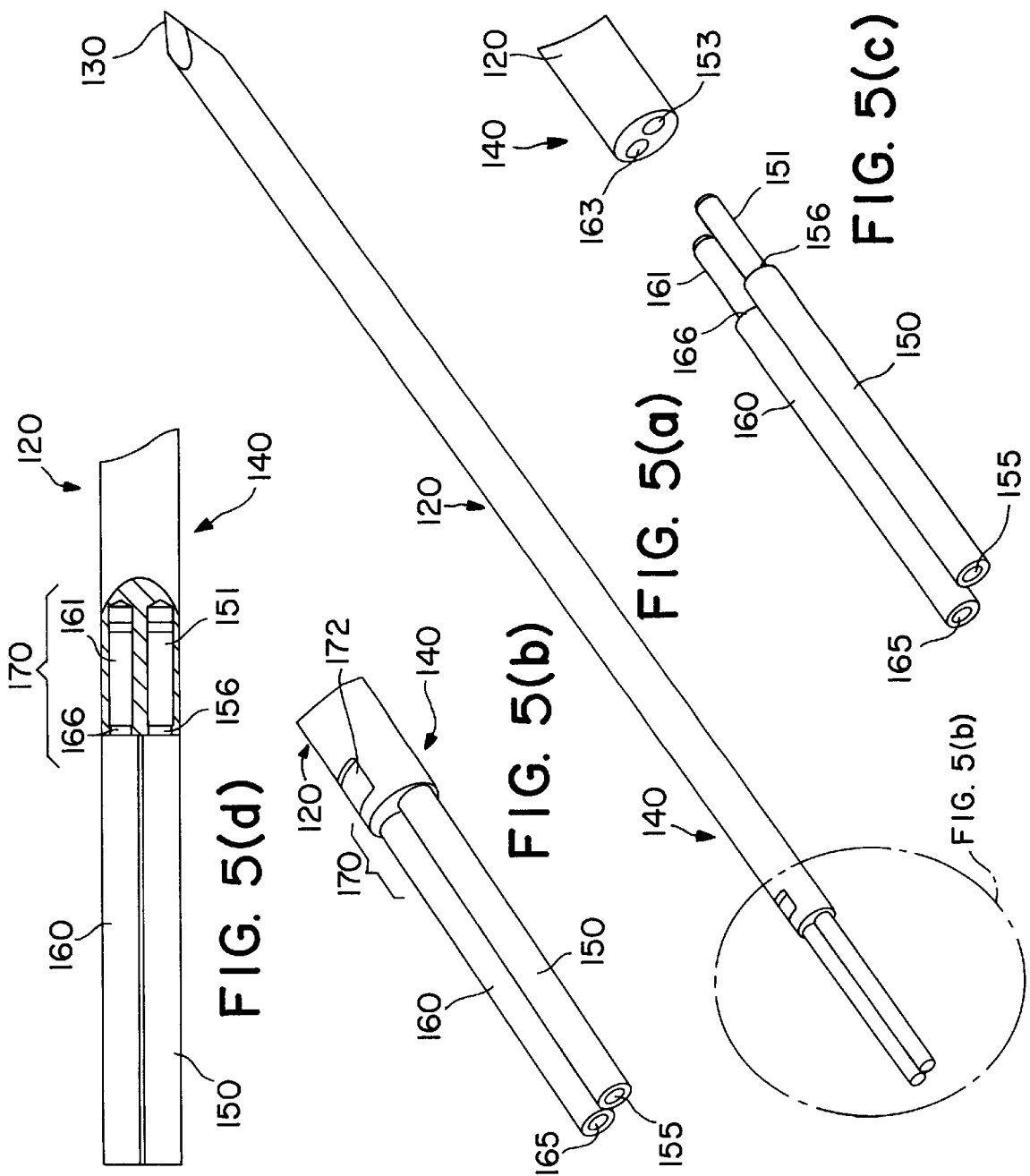

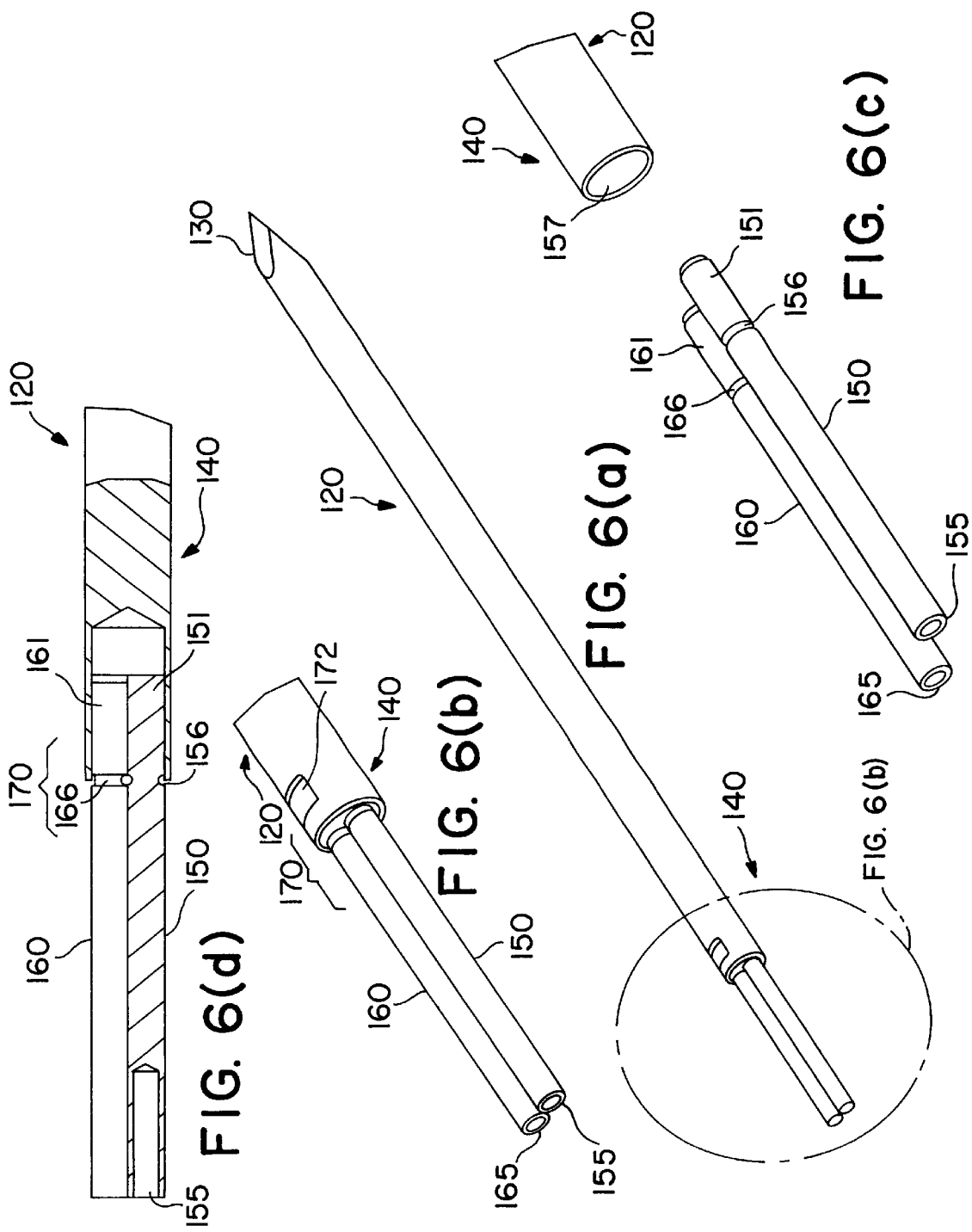

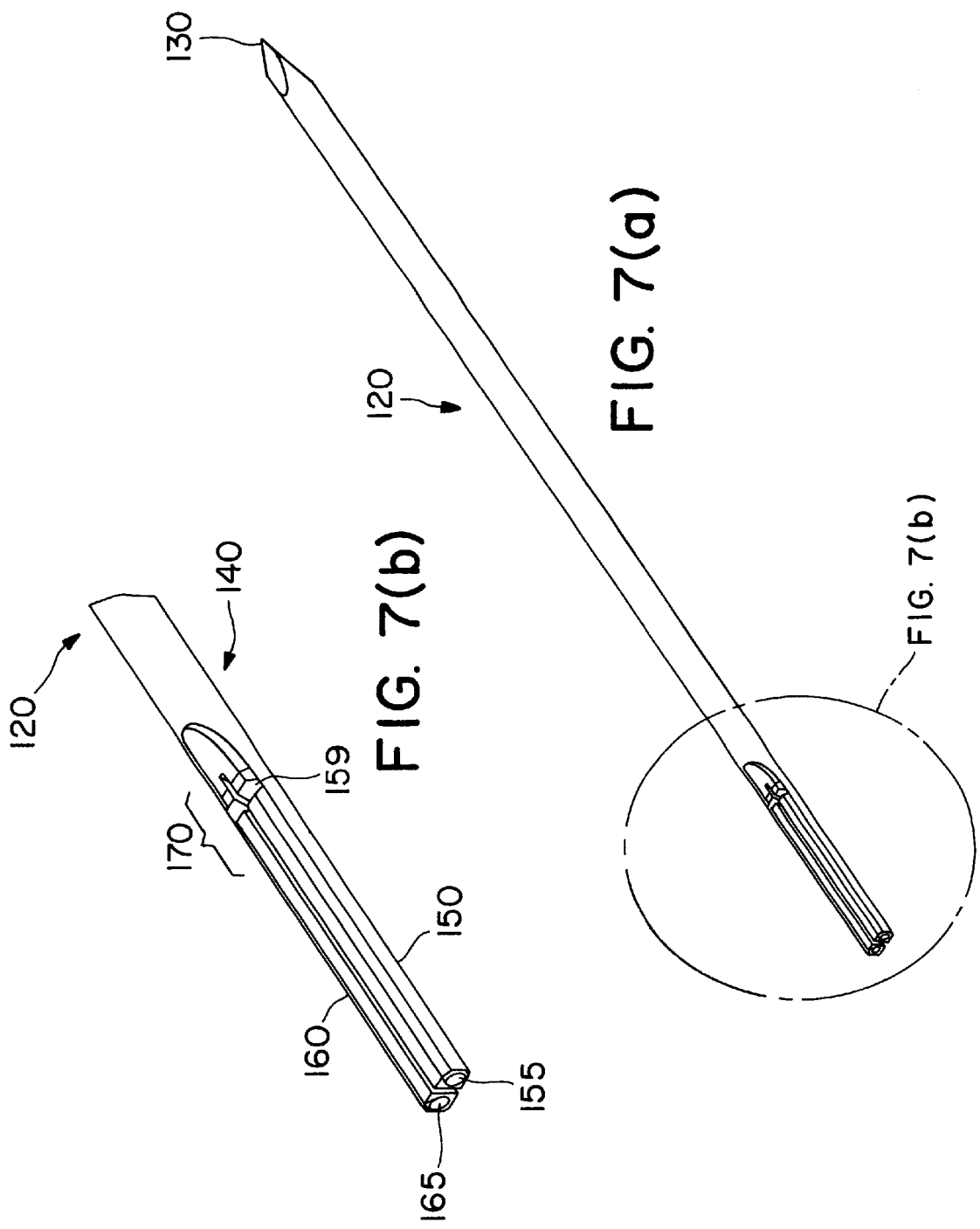

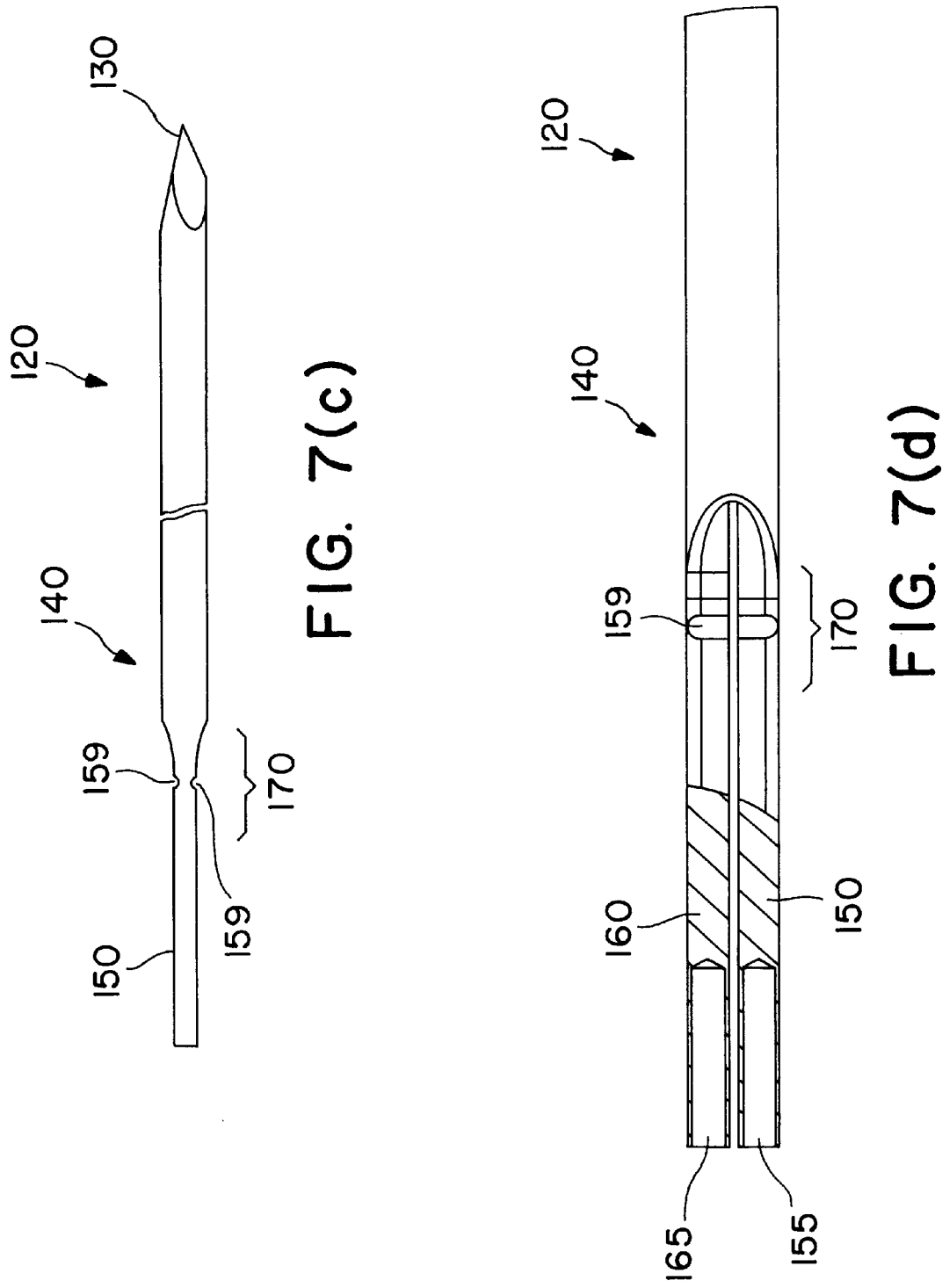

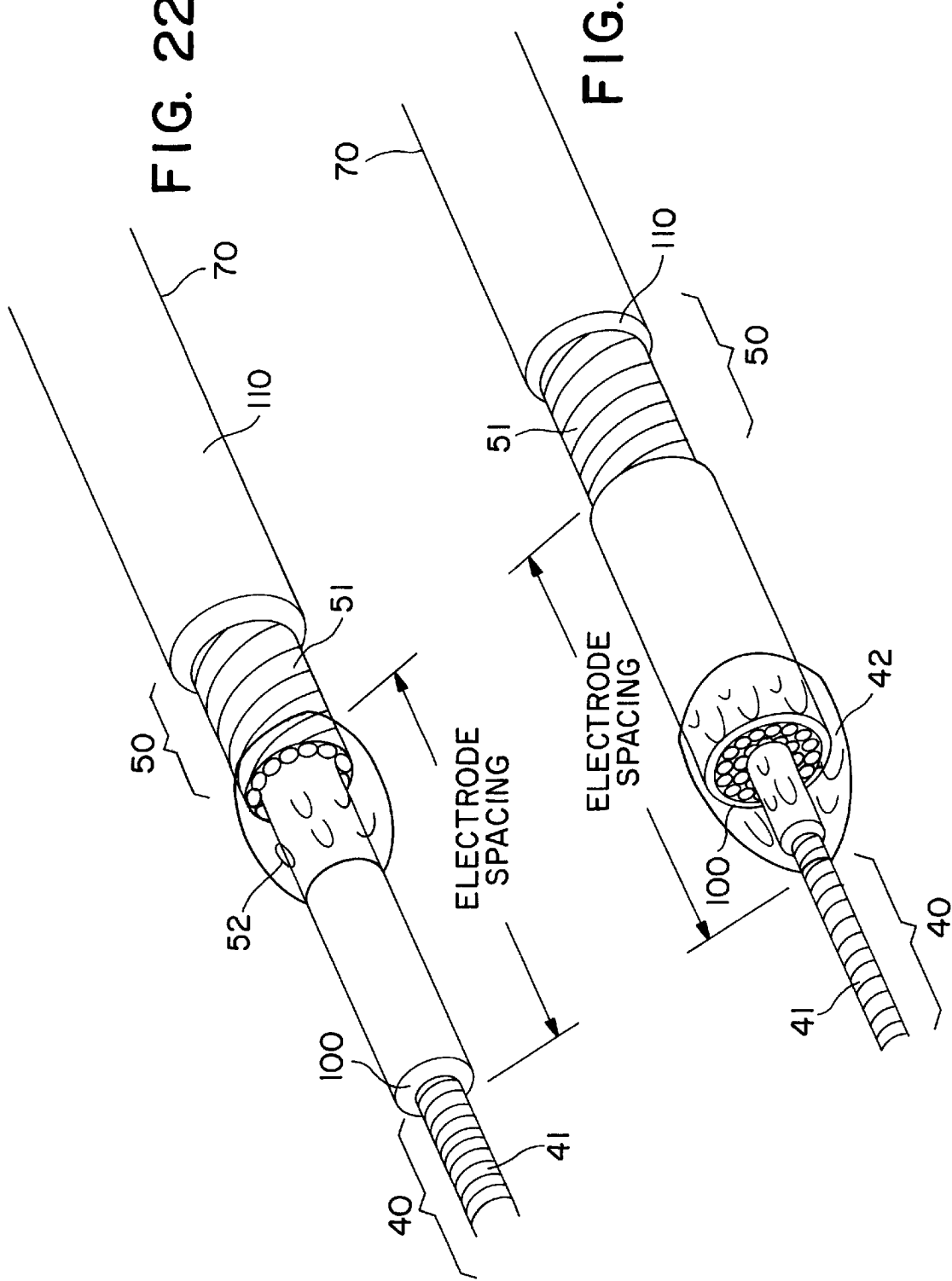

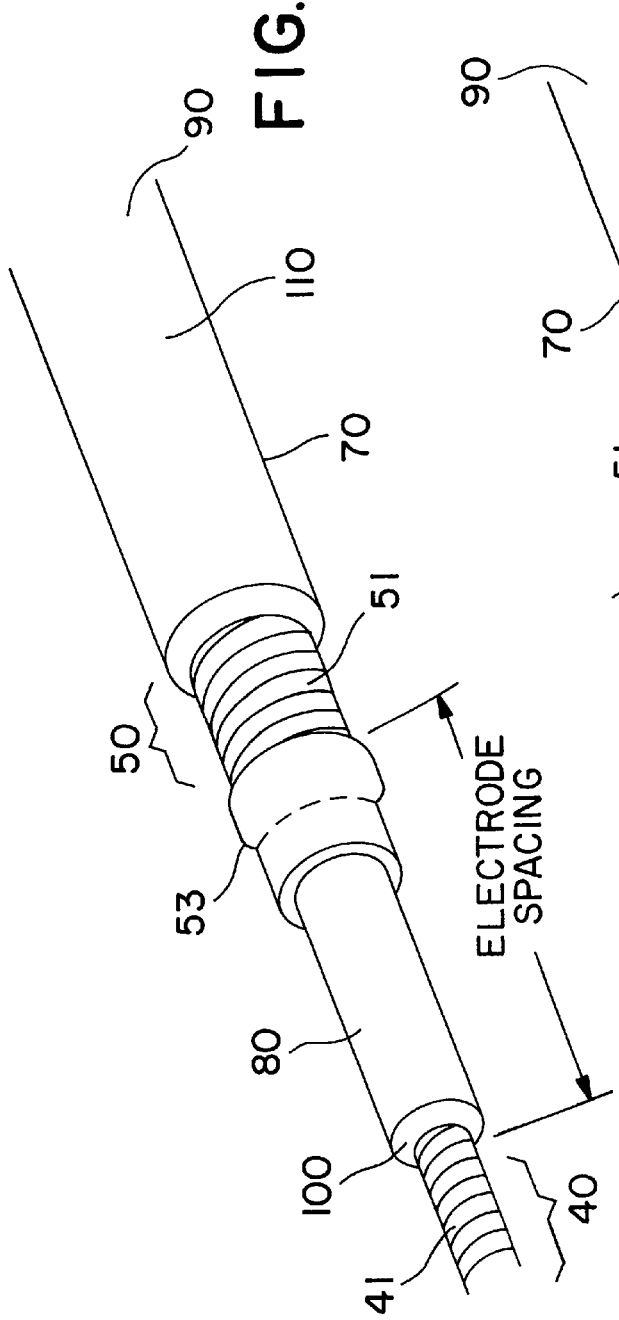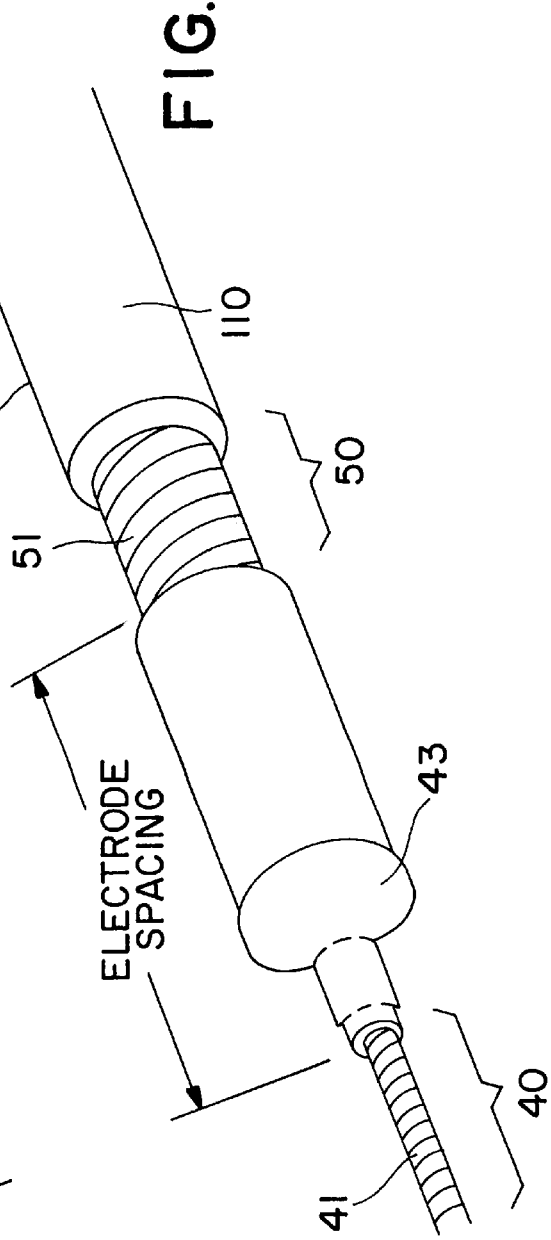

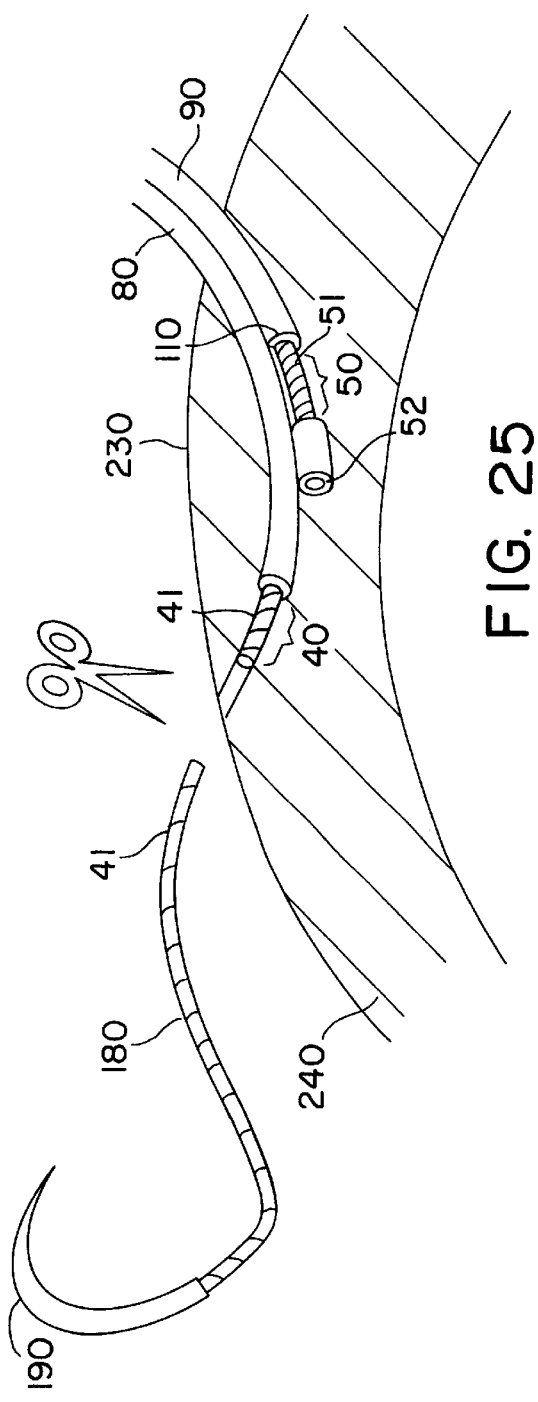
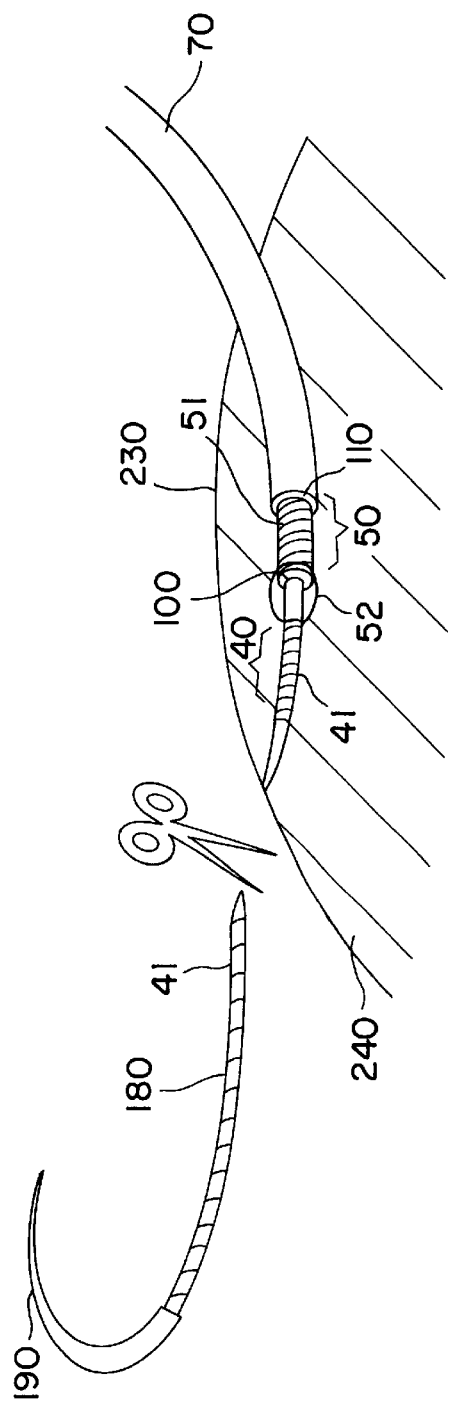

TEMPORARY BI-POLAR HEART WIRE

FIELD OF THE INVENTION

The present invention relates generally to heart wires and leads, and more particularly to temporary bipolar heart wires and leads for pacing, defibrillating and monitoring.

BACKGROUND OF THE INVENTION

Unipolar and bipolar surgically implanted temporary heart wires are well known in the art, some examples of which may be found in the issued U.S. Patents listed in Table 1 below.

TABLE 1

Prior Art Patents

| U.S. Pat. No. | Title |
|---|---|
| 3,035,583 | Conductive Sutures |
| 3,125,095 | Flexible Stainless Steel Sutures |
| 3,664,347 | Electric Heart Stimulation Method and Electrode |
| 3,949,756 | Sutures with Notch Near Needle-Suture Junction |
| 4,101,756 | Heart Pacer Lead Wire with Break-Away Needle |
| B14,010,756 | Heart Pacer Lead Wire with Break-Away Needle |
| 4,054,144 | Short-Crimp Surgical Needle |
| 4,338,947 | Positive Fixation Heart Wire |
| 4,341,226 | Temporary Lead with Insertion Tool |
| 4,442,840 | Electrical Connector Apparatus and Method for a Temporary Cardiac Pacing Wire |
| 4,444,207 | Method of Anchoring a Temporary Cardiac Pacing Lead |
| 4,530,368 | Temporary Bipolar Pacing Lead |
| 4,541,440 | Bipolar Epicardial Temporary Pacing Lead |
| 4,553,554 | Electrical Lead and Method for Temporary Cardiac Pacing |
| 4,630,617 | Heart Pacer Lead Wire with Pull-Away Needle |
| 4,633,880 | Surgical Electrode |
| 4,693,258 | Surgical Electrode for Cardiac Pacing and Monitoring |
| 4,972,833 | Epicardial Pacing Lead |
| 5,217,027 | Temporary Cardiac Lead |
| 5,241,957 | Bipolar Temporary Pacing Lead and Connector and Permanent Bipolar Nerve Wire |
| 5,314,463 | Bipolar Nerve Electrode |
| 5,350,419 | Cardiac Pacing Lead |
| 5,423,876 | Intramuscular Lead Having Improved Insertion |
| 5,792,217 | Temporary Bipolar Heart Wire |

All patents listed in Table 1 hereinabove are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the teachings of the present invention.

Surgically implanted temporary heart wires for use as heart pacer and monitoring electrodes are well known in the medical profession. In general, such a heart wire is constructed of a number of fine, stainless steel wires twisted together to form a single, flexible, multifilament electrode wire. The major portion of the wire is typically insulated with a polyethylene, polytetrafluoroethylene, silicone, nylon, or other suitable electrically nonconductive and biocompatible materials, with a short length of wire at either end left uninsulated.

To one uninsulated end of such an electrode wire there is generally attached by swaging or other means a fine curved needle for piercing the heart tissue to place the uninsulated end of the electrode in the myocardium or epicardium. At the other end of such an electrode wire there is generally affixed a Keith-type cutting needle for piercing the thoracic wall to lead the electrode to an outer point for connection with the pacemaker. Once the electrode has been properly positioned, the curved needle and the Keith-type needle are typically clipped off and the uninsulated end of the electrode is ready for attachment to a pacemaker or monitoring device.

Some prior art unipolar heart wires have break-away Keith-type needles attached to their proximal ends, where no clipping is required to remove the needle from the heart wire. Other prior-art Keith-type breakaway needles require the use of, or most preferably employ, an external adapter or transition box for breaking the needle in the appropriate location and facilitating attachment of electrical conductors in the lead to an external electrical apparatus. See, for example, the bipolar heart wire and corresponding external connector disclosed in U.S. Pat. No. 5,241,957, where the external connector is required to establish electrical connection between an EPG or PSA and the heart wire.

Many known heart wires are characterized in having one of the two following disadvantages. First, when some known unipolar heart wires are used in applications requiring two electrodes, two different, separate heart wires must be attached to the heart in two separate procedures. Attaching two such heart wires consumes valuable time at a critical stage in heart surgery. Second, when some known bipolar heart wires are used, the needle attached to the proximal end of the heart wire for piercing the transthoracic wall must be clipped off with a scissors or other tool, and pin connectors must be attached to the resulting bare separate wires for establishing electrical connection to an external pacemaker or external electrical apparatus. These steps of needle removal and wire attachment are separate, time consuming acts, and also occur at a critical stage in heart surgery. Moreover, upon repeated attachment, removal and reattachment, the ends of the stainless steel wire may fray and become difficult to work with.

What is needed is a heart wire that attaches easily and quickly to the heart but which also has convenient, easy-to-use connectors disposed between the proximal end of the heart wire and an external pulse generator (EPG), pacing system analyzer (PSA), defibrillator or other such external electrical apparatus. Most preferably, the heart wire should not require substantial electrical or mechanical manipulations by the surgeon, should be comfortable to the patient, and should establish secure and reliable electrical contacts. Finally, the heart wire should be reasonably economical to manufacture.

SUMMARY OF THE INVENTION

The present invention has certain objects. That is, the present invention provides solutions to problems existing in the prior art. It is an object of the present invention to provide a surgical electrode having a needle, the sharpened proximal end of which can be removed without cutting. It is a further object of this invention to provide a surgical electrode which is quickly and easily attached to an external electrical apparatus after the sharpened end of the needle has been removed. It is yet a further object of this invention to provide surgical electrodes having electrical connecting means adapted for specific electrical devices.

The present invention has certain advantages. More particularly, the heart wire of the present invention: (a) reduces patient trauma; (b) reduces the number of puncture sites in the myocardium or epicardium; (c) reduces the number of puncture sites in the thorax; (d) is easy to use; (e) permits two electrodes to be implanted quickly during a critical stage of heart surgery; (f) has electrodes spaced a predetermined optimal distance apart for sensing and pacing applications; (g) attaches to external pacemakers, defibrillators, monitoring equipment and other external electrical apparatus quickly, easily, securely and reliably; (h) does not require lead wires to be clipped with scissors; (i) requires no use of an external, separate adapter or transition box for separating or breaking the needle from the connectors; (1) requires no use of an external, separate adapter or transition box for establishing electrical connection between the electrodes and an external electrical apparatus; (k) prevents the distal ends of electrode wires from becoming frayed; (l) has fewer parts than many prior art heart needles; (m) is less expensive to manufacture; (n) helps reduce health care costs, and (o) increases patient safety owing to shortened implantation times and quicker connection to external pacing, defibrillating or monitoring equipment.

The heart wire and needle of the present invention have certain features, including one or more of the following: (a) a chest needle having a pointed or proximal end and a blunt or distal end, the blunt end being breakingly, snappingly, crimpingly, compressionally, slidingly, elastically, glueingly, viscously, vacuumingly or otherwise attached separably to the proximal ends of at least two connectors; (b) at least two connectors that upon being separated from the blunt end of the needle form pins or other structures suitable for fitting in or otherwise appropriately engaging an external connector configured to receive the connectors, where the external connector is attached to an external electrical apparatus for monitoring, pacing or defibrillating the heart; (c) a curved, straight or otherwise shaped needle disposed at the distal end of the heart wire that is suitable for piercing the myocardium or epicardium, and (d) two or more electrodes located between the distal and proximal ends of the heart wire for pacing, defibrillating or monitoring the heart, the electrodes being formed of exposed portions of bare wire, wherein overlying insulation has been removed.

In one preferred embodiment, the present invention is a temporary bipolar lead having a proximal and a distal end, and comprises a chest needle at its proximal end, the needle having a proximal pointed end and a distal blunt end attached to at least two connectors by a weakened zone. At least two pacing, sensing or defibrillating proximal and distal electrodes are disposed near the distal end of the lead, and a coil affixation member may optionally be formed by one of the electrodes. The two or more electrodes are preferably formed of bare wire electrically and mechanically connected to respective electrical conductors. The proximal electrode is most preferably formed of a portion of bare wire. The distal ends of the at least two electrical conductors form the electrodes, and also extend between the electrodes and the connectors.

Other objects, features, advantages and embodiments of the present invention will become apparent upon reading the detailed description and the claims.

BRIEF DESCRIPTION OF THE DRAWINGS

FIG. 5(a) shows a perspective view of a first preferred embodiment of the chest needle of the present invention;

FIG. 5(b) shows an enlarged view of the distal end of the chest needle of FIG. 5(a);

FIG. 5(c) shows an enlarged view of the connectors of FIG. 5(a) prior to the distal ends thereof being inserted in the blunt end of the needle;

FIG. 5(d) shows an enlarged cross-sectional view of the weakened zone of the chest needle of FIG. 5(a);

FIG. 6(a) shows a perspective view of a second preferred embodiment of the chest needle of the present invention;

FIG. 6(b) shows an enlarged view of the distal end of the chest needle of FIG. 6(a);

FIG. 6(c) shows an enlarged view of the connectors of FIG. 6(a) prior to the distal ends thereof being inserted in the blunt end of the needle FIG. 6(d) shows an enlarged cross-sectional view of the weakened zone of the chest needle of FIG. 6(a);

FIG. 7(a) shows a perspective view of a third preferred embodiment of the chest needle of the present invention FIG. 7(b) shows an enlarged view of the distal end of the chest needle of FIG. 7(a);

FIG. 7(c) shows a side view of the chest needle of FIG. 7(a);

FIG. 7(d) shows an enlarged cross-sectional view of the weakened zone of the chest needle of FIG. 7(a);

FIGS. 22(a) and 22(b) show enlarged perspective views of two embodiments of the distal end of the lead shown in FIG. 21;

FIGS. 23(a) and 23(b) show enlarged perspective views of two different embodiments of the distal end of the lead shown in FIG. 21;

FIG. 25 shows a preferred embodiment of the present invention similar to those illustrated in FIGS. 18, 19 and 20(a) through 20(c), where both electrodes are positioned within the ventricular myocardium, and FIG. 26 shows a preferred embodiment of the present invention similar to those illustrated in FIGS. 21, 22(a), 22(b), 23(a) and 23(b), where both electrodes are positioned within the ventricular myocardium.

DETAILED DESCRIPTION OF THE PREFERRED EMBODIMENTS

In the Figures and the Detailed Description, like numbers refer to like elements, components and parts throughout.

This application hereby incorporates by reference herein, in its entirety, U.S. patent application Ser. No 08/818,069 to Camps et al. for "Temporary Bipolar Heart Wire" filed Mar. 14, 1997.

As used in the specification and claims hereof, the following terms have the particular meanings and definitions set forth below.

The terms "temporary heart wire", "temporary heart lead" and any substantially similar variants thereof mean a temporary heart lead or wire introduced surgically through the myocardium or epicardium from the exterior of the heart, where the lead or wire has at least one electrode near its distal end for monitoring, pacing or defibrillating the heart at or near a myocardial or epicardial site, and where the lead or wire has at least one connector or needle near its proximal end for electrical connection to an external pacing, monitoring, or defibrillating apparatus." The terms "heart wire, heart lead" and any substantially similar variants thereof are synonymous.

The term "proximal" means that portion of an apparatus, or component or element of an apparatus, disposed in closer proximity to the end of the wire remaining outside a patient's body following the lead implantation procedure than it is to the end of the wire implanted in or attached to the heart.

The term "distal" means that portion of an apparatus, or component or element of an apparatus, disposed in closer proximity to the end of the wire that is inserted through or attached first to the myocardium or epicardium during a wire implantation procedure than it is to the end of the wire that remains outside the patient's body following the lead implantation procedure.

The term "chest needle" or "needle" means the proximal end of the heart wire of the present invention, and includes the pointed end of the needle, and the shank and body thereof, or may mean the needle disposed at the distal end of the lead of the present invention, a piercing means, or a means for piercing, depending on the particular context in which the term "needle," "piercing means," or "means for piercing" appears. Additionally, needle 120 may include the weakened zone of the needle intermediate between the blunt end of the needle and the connectors, and may also include the connectors attached to the weakened zone or the blunt end.

The term "blunt" means the shank of the needle and that portion of the chest needle disposed proximally of the connectors and in proximity thereto. The blunt portion of the needle may include further that portion of the needle connected directly to the proximal ends of the connectors.

Figure 1:
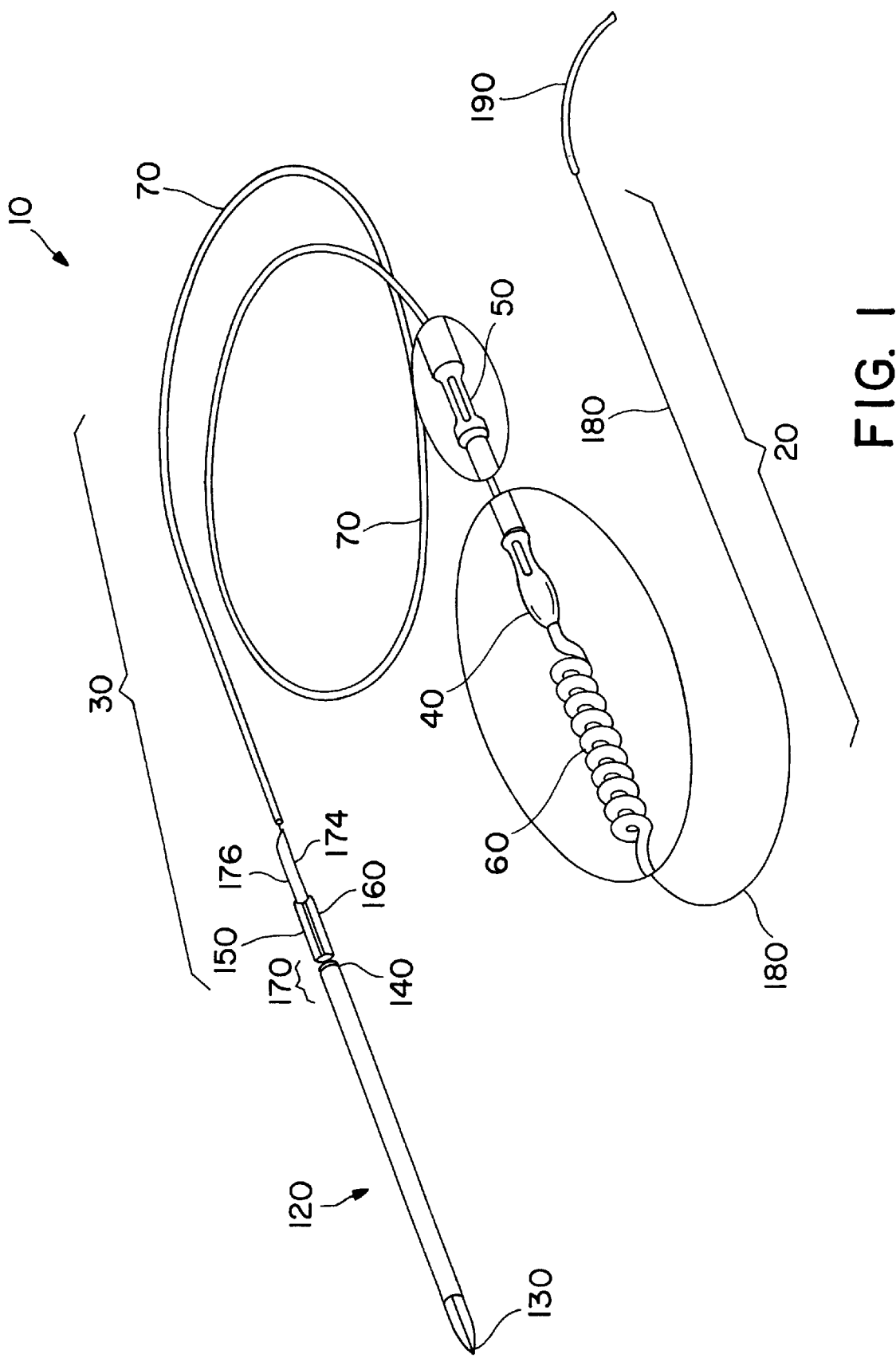
FIG. 1 shows a perspective view of one embodiment of a prior art lead.

FIG. 1 shows a perspective view of a preferred embodiment of the present invention designed specifically for pacing and sensing applications. Heart lead or wire 10 has distal end 20 and proximal end 30, and most preferably comprises needle 120, connectors 150 and 160, weakened zone 170, coaxial conductor or lead body 70, proximal electrode 50, distal electrode 40, coil affixation member 60, strand 180 and curved atraumatic needle 190.

Strand 180, preferably formed of polypropylene and constituting a monofilament, forms coil affixation member 60, attaches to distal electrode 40 and extends to atraumatic curved needle 190. Coil affixation member 60 may be similar to the type of coil disclosed in U.S. Pat. No. 4,341,226. Coil 60 ensures secure temporary fixation of wire 10 in the heart and prevents dislodgments which might otherwise occur were a smooth tipped lead employed. Most preferably, one length of polypropylene comprises coil 60 and strand 180. More than one curved needle 190 may be attached to distal end 20 of lead 10. For example, each conductor of lead body 70 may terminate in a separate curved needle.

Lead body 70 may comprise any pair of suitable flexible electrical conductors, such as coaxial conductors or so-called "lamp cord" or "zip-cord" (e.g., side-by-side) conductors. Most preferably, lead body 70 is a coaxial pair of inner and outer electrical conductors, where the conductors are formed of helically wound strands of multifilament or twisted stainless steel. Lead body 70 most preferably comprises conductors that provide a high degree of flexibility and superior mechanical and electrical properties.

Electrodes 40 and 50 are preferably formed of medical grade stainless steel suitable for temporary applications, and are preferably spaced a predetermined distance apart known to optimize the delivery of pacing pulses or the detection and sensing of cardiac electrical signals. Distal electrode 40 is mechanically and electrically connected by inner or first conductor 80 (not shown in FIG. 1 but shown in FIGS. 9, 11 and 12) to first connector 150 at the proximal end of lead 10, which, in turn, is mechanically connected to blunt end 140 of needle 120 by weakened zone 170. Proximal electrode 50 is mechanically and electrically connected by outer or second conductor 90 (not shown in FIG. 1 but shown in FIGS. 9, 11 and 12) to second connector 160 at the proximal end of lead 10, which is also, in turn, mechanically connected to blunt end 140 of needle 120 by weakened zone 170.

Needle 120, most preferably of the atraumatic type, is a chest needle for piercing the thorax, and has pointed end 130 and blunt end 140. Needle 120 is preferably substantially straight between pointed end 130 and blunt end 140. Pointed end 130 has a cutting edge designed for piercing the thoracic wall of the patient. Blunt end 140 attaches breakingly, snappingly, crimpingly, compressionally, adhesively, glueingly, elastically, slidingly or in otherwise suitable connecting yet separable fashion to the proximal ends of connectors 150 and 160. Weakened or pull-apart zone 170 separates the proximal ends of connectors 150 and 160 from blunt end 140. Connectors 150 and 160 most preferably form cylindrically shaped pin connectors having circular cross-sections upon being separated from blunt end 140. Other structural configurations of connectors 150 and 160 fall within the scope of the present invention and include, but are not limited to, pin-shaped connectors having rectangular or square cross-sections, reed-shaped connectors, and flexible connectors.

Figure 2:
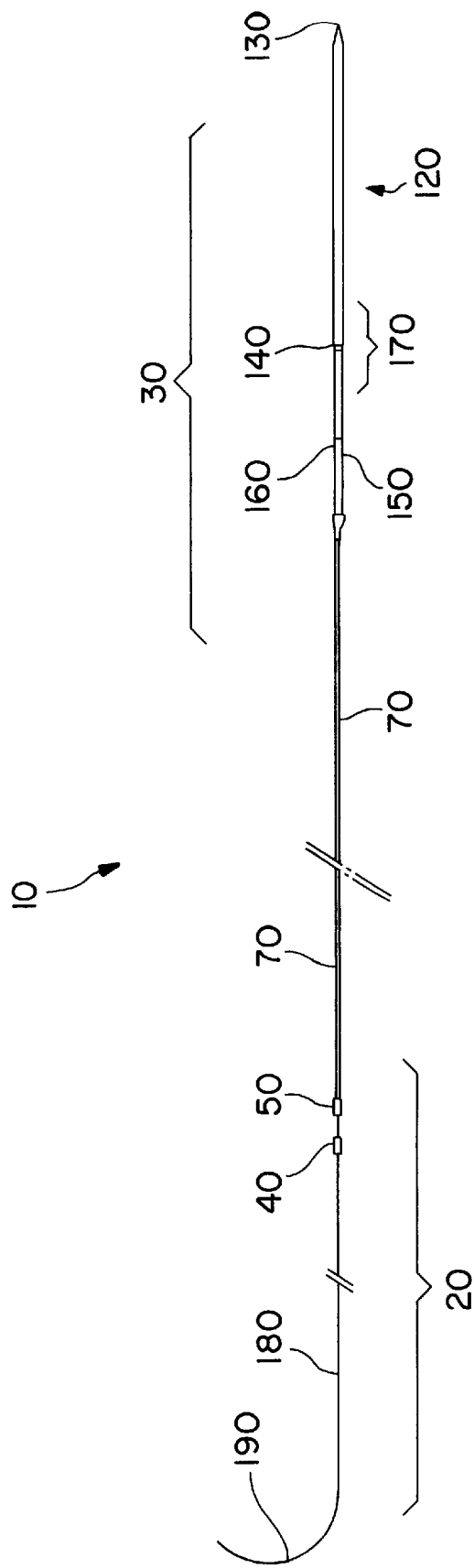
FIG. 2 shows a side view of the lead of FIG. 1.

Lead 10 includes curved needle 190 for piercing the myocardium or epicardium preparatory to drawing the heart wire 10 and its electrodes within the myocardium or epicardium. The proximal end of curved needle 190 is connected to strand 180. FIG. 2 shows a side view of the lead of FIG. 1. Note that coil 60 is shown in FIG. 1, but is not shown in FIG. 2. Coil 60 is an optional component of the present invention, and is not required for the practice thereof. For example, the distal end of lead 10 may be secured to the myocardium or epicardium with sutures instead of coil 60.

Figure 3:
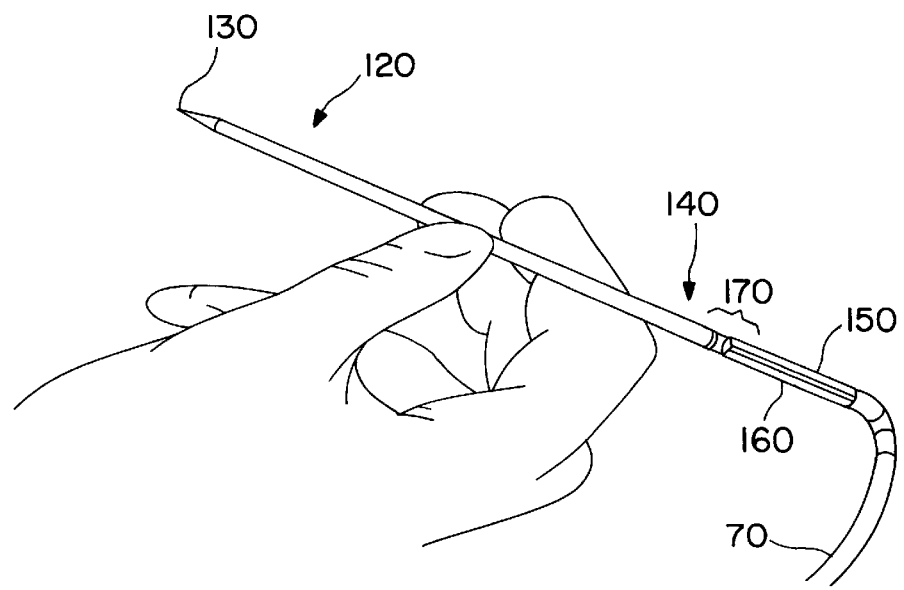
FIG. 3 shows a perspective view of the proximal end of a preferred embodiment of the present invention.

FIG. 3 shows a perspective view of the proximal end of a preferred embodiment of lead 10. After the surgeon attaches the distal end of lead 10 to the myocardium or epicardium using curved needle 190 and some means for securing the electrodes thereto such as coil 60, needle 120 pierces the patient's thorax and is brought outside the patient's chest.

Figure 4:
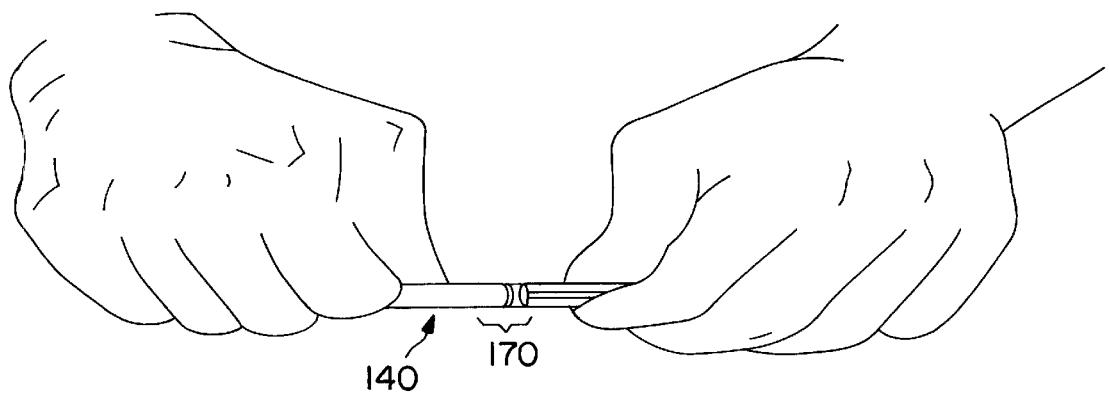
FIG. 4 shows a perspective view of a preferred method of manually applying force to a preferred embodiment of the present invention to cause the connectors to separate from the blunt end.

When the electrodes have been positioned suitably in the myocardium or epicardium and lead 10 is ready for attachment to an external electrical apparatus such as an EPG, needle 120 is snapped at weakened zone 170 as shown in FIG. 4 by applying a bending moment about zone 170. FIG. 4 shows a perspective view of a preferred method of applying force manually to a preferred embodiment of lead 10 to cause the weakened zone to fail structurally, and to thereby separate the connectors 150 and 160 from blunt end 140. The snapped off portion of the needle is discarded while connectors 150 and 160 are readily inserted into a properly sized receptacle in the EPG or other external electrical apparatus. Connectors 150 and 160 are structures having standardized dimensions, and are configured to permit attachment, removal, and reattachment to an external electrical apparatus in quick, ready, reliable, secure and safe fashion as required, and without encountering frayed ends characteristic of bare, multifilament stainless steel wires.

The present invention permits reliable and secure electrical connections to be established securely, reliably, quickly and safely between at least two electrodes and the external electrical apparatus without the use of a separate connector housing such as that disclosed in U.S. Pat. No. 5,241,947. A separate connector housing adds extra cost to heart wire system. A separate connector housing also increases the likelihood of electrical connection failures occurring between lead 10 and the external electrical apparatus to which lead 10 is connected because the housing contains additional electrical junctions and points of connection not present in the invention. Additionally, a housing like that disclosed in the foregoing '947 patent increases the complexity of, and time required to complete, a heart wire implant procedure. Thus, the present invention may simplify implant procedures, reduce the amount of time required to complete such procedures, and increase the reliability and safety of the heart wire system respecting prior art heart wire systems.

FIGS. 5(*a*) through 5(*d*) show different views of a first preferred embodiment of chest needle 120 of the present invention. Reduced diameter pins 151 and 161 are integral to electrically conductive, stainless steel, cylindrically-shaped pin connectors 150 and 160, and extend from the proximal ends thereof. Regions 156 and 166 are scored mechanically, and are disposed between pins 151 and 161 and the proximal ends of connectors 150 and 160. Scoring provides the user with a means of visually identifying the region where the connectors will break. After pins 151 and 161 are fitted into corresponding recesses 153 and 163 disposed within blunt end 140, pins 151 and 161 are swaged or preferably crimped in place by at least one crimp 172, and more preferably by two crimps disposed on opposing sides of needle 120.

The proximal ends of conductors 80 and 90 (not shown in FIGS. 5(*a*) through 5(*d*)) slide within recesses 155 and 165 and are crimped in place, thus establishing electrical and mechanical connections between the conductors and the connectors.

Weakened zone 170 preferably comprises the proximal ends of connectors 150 and 160, scored regions 156 and 166, blunt end 140, pins 151 and 161 and recesses 153 and 163. Connectors 150 and 160 separate from needle 120 at scored regions 156 and 166 when a bending moment is applied to weakened zone 170.

Weakened zone 170 may be formed by methods other than scoring. For example, zone 170 may be formed by machining, forming a groove by rotating the connectors or needle in contact with a cutting wheel, or by cutting a notch or forming a crimp on one or both sides of the connectors or the needle. A groove machined or scored in connectors 150 and 160 or pins 151 and 161 reduces the diameter of needle 120 and therefore reduces the strength of needle 120 in weakened zone 170.

Weakened zone 170 may be formed in ways that do not require connectors 150 and 160 to break in certain regions. For example, the amount of force applied when forming crimp 172 may be adjusted so that connectors 150 and 160 may be pulled out of blunt end 140 manually or when a special removal tool is used. Alternatively, pins 151 and 161 may have diameters sized to frictionally engage the inner sidewalls of recesses 155 and 165 with sufficient force to prevent their removal therefrom until a predetermined amount of outward force is applied to pull connectors 150 and 160 from blunt end 140.

Less preferably, weakened zone 170 may be formed by gluing or binding pins 151 and 161 in recesses 153 and 163 using a suitable biocompatible adhesive or viscous material so that a user may pull connectors 150 and 160 out of blunt end 140 when a sufficiently large predetermined force is applied thereto.

Weakened zone 170 may also be obtained by modification of crystalline structure through heat treating by drawing the needle to create a necked down segment, annealing weakened zone 170, or by any other convenient or suitable means.

Grooved or otherwise weakened zone 170 of needle 120 may be located at any convenient distance from blunt end 140. The lengths of the connectors remaining after the pointed end is snapped off should be sufficient for grasping and inserting the connectors into an electrical receptacle. In general, weakened zone 170 is preferably at least 1 centimeter from the distal ends of the connectors or the pointed end 130 of needle 120. Most preferably this distance is between about 2 and 3 centimeters. When the distance between weakened zone 170 and pointed end 130 is less than about 1 centimeter, it becomes difficult to grasp needle 120 for breaking. When connectors 150 and 160 are less than 1 centimeter long, it becomes difficult to handle and insert the connectors into electrical receptacles.

Needle 120 may be curved, straight, or of any other desired, suitable configuration. Pointed end 130 may have any desired cross-sectional configuration. While a triangular cross-section is generally preferred, pointed end 130 may also be circular, triangular, rectangular, square or any other suitable shape in cross-section. Connectors 150 and 160 may also be circular, triangular, rectangular, square or any other suitable shape in cross-section. Such connector cross-sections may find particular use where the connectors are intended to be connected to a particular external electrical apparatus and no other.

Since connectors 150 and 160 establish electrical connection with an external electrical apparatus, insulation 100 and 110 (not shown in FIGS. 5(a) through 5(d)) may extend up to or even over the distal ends of connectors 150 and 160. Abutting the insulation to a location near blunt end 140 and heat shrinking and sealing the joint may provide the advantage of a smooth, continuous and sealed exterior surface that facilitates threading needle 120 through the thoracic wall. In some connectors of the prior art, it has been necessary to provide a segment of uninsulated wire or connector adjacent the needle to allow for electrical connection to an external electrical apparatus after the needle has been clipped off the wire, or to take an extra step of stripping insulation from the wire to provide an electrical connection.

FIGS. 6(a) through 6(d) show different views of a second preferred embodiment of the chest needle of the present invention. Pins 151 and 161 are integral to electrically conductive, stainless steel, cylindrically-shaped pin connectors 150 and 160, and extend from the proximal ends thereof. Regions 156 and 166 are scored mechanically. Blunt end 140 is preferably compressed slightly in the vicinity of axial recess 157 and in a vertical direction to increase the horizontal dimension of axial recess 157 to ease the insertion of pins 151 and 161 therein. Following insertion of pins 151 and 161 in recess 157, blunt end 140 is crimped to form at least one crimp 172, and more preferably two crimps disposed on opposing sides of needle 120.

The proximal ends of conductors 80 and 90 (not shown in FIGS. 6(a) through 6(d)) slide within recesses 155 and 165 and are crimped in place at crimps 154 and 164 (shown in FIG. 12), thus establishing electrical and mechanical connections between the conductors and the connectors.

Weakened zone 170 preferably comprises the proximal ends of connectors 150 and 160, scored regions 156 and 166, blunt end 140, pins 151 and 161 and axial recess 157. Connectors 150 and 160 separate from needle 120 at scored regions 156 and 166 when a bending moment is applied to weakened zone 170.

Weakened zone 170 may be formed in ways that do not require connectors 150 and 160 to break in certain regions. For example, the amount of force applied when forming crimp 172 may be adjusted so that connectors 150 and 160 may be pulled out of blunt end 140 manually or when a special removal tool is used. Alternatively, pins 151 and 161 may have diameters sized to frictionally engage the inner sidewall of axial recess 157 with sufficient force to prevent their removal therefrom until a predetermined amount of outward force is applied to pull connectors 150 and 160 from blunt end 140.

FIGS. 7(a) through 7(d) show different views of a third preferred embodiment of the chest needle of the present invention. Connectors 150 and 160 are integral to and form the distal portion of electrically conductive, stainless steel needle 120. Notches 159 are machined in the top and bottom surfaces of connectors 150 and 160 to form weakened zone 170.

Less preferably, weakened zone 170 consists of only one notch 159. The proximal ends of conductors 80 and 90 (not shown in FIGS. 7(a) through 7(d)) slide within recesses 155 and 165 and are preferably crimped in place, thus establishing electrical and mechanical connections between the conductors and the connectors. Connectors 150 and 160 separate from needle 120 at notches 159 when a bending moment is applied to weakened zone 170.

Figure 8:
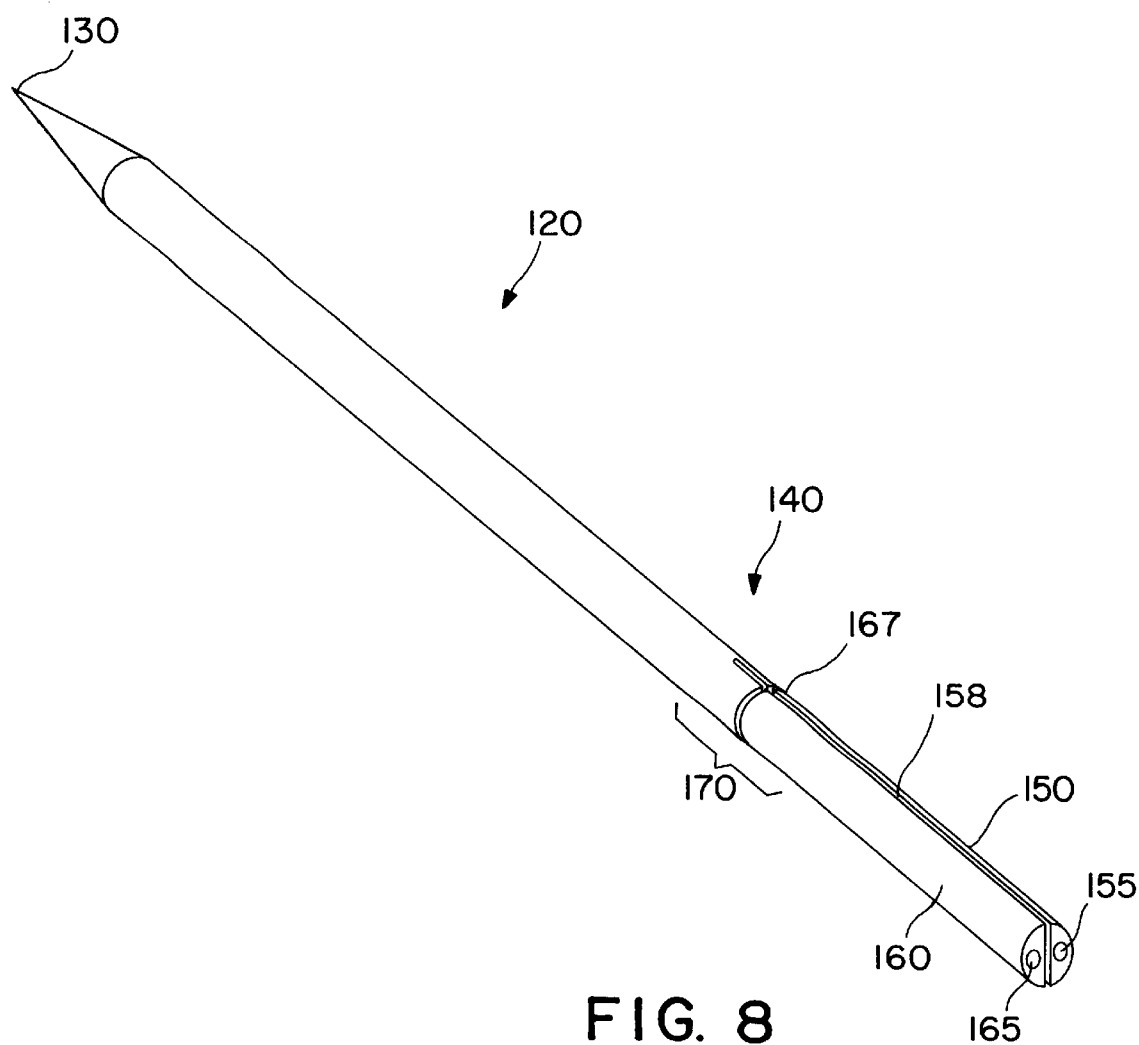
FIG. 8 shows a perspective view of a fourth preferred embodiment of the chest needle of the present invention.

FIG. 8 shows a perspective view of a fourth preferred embodiment of the chest needle of the present invention. Needle 120 and connectors 150 and 160 are machined, forged or otherwise formed of a single piece of stainless steel. Longitudinal groove 158 separates conductor 150 from conductor 160 along their respective entire lengths except near the intersection of blunt end 140, circumferential groove 167 and longitudinal groove 158, where conductors 150 and 160 are attached to blunt end 140 by a zone of reduced diameter stainless steel. Connectors 150 and 160 separate from needle 120 at circumferential groove 167 when a bending moment is applied to weakened zone 170.

Figure 9:
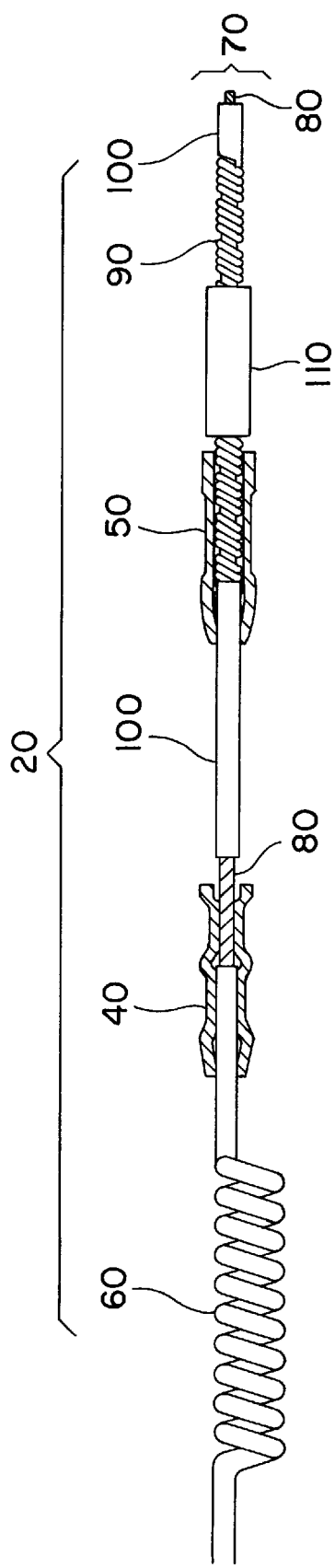
FIG. 9 shows an enlarged cross-sectional view of a portion of the distal end of a preferred embodiment of the present invention.

FIG. 9 shows an enlarged cross-sectional view of the distal end of one embodiment of the present invention, where lead 10 is designed specifically for pacing and sensing applications. FIG. 9 shows affixation coil 60 and electrodes 40 and 60 in greater detail. Affixation coil 60 preferably includes ten right hand wound turns and is crimpingly affixed to tip electrode 40. Inner conductor 80 is covered by inner insulation 100. Electrode 50 is crimpingly affixed to outer conductor 90 which is covered by outer insulation 110.

The two conductors of coaxial wire 70 preferably comprise twisted and helically wound strands of medical grade stainless steel wire. Less preferably those conductors may be formed of single strands of stainless steel, or of one or more strands of electrically conductive polymeric material. Inner or first conductor electrical insulation 100 is most preferably formed of fluorinated ethylene propylene (FEP), polytetrafluorethylene (PTFE), or any other suitable medical grade, biocompatible dielectric insulating coating such co-polymer polytetrafluorethylene, polyethylene, silastic, neoprene, polypropylene, or polyurethane. Inner insulation 100 covers and insulates inner conductor 80, which is preferably composed of 19 twisted, wound, or twisted and wound stainless steel filaments or strands.

Outer conductor 90 is preferably composed of 26 to 40 medical grade stainless steel strands or filaments, and most preferably 32 such strands, wound in helical fashion over inner insulation 80. Helical winding of the outer conductors imparts a high degree of flexibility to lead 10. Inner electrical insulation 100, disposed between the inner and outer electrical conductors, may be. Outer or second conductor electrical insulation 110 is preferably formed of FEP or polyethylene, or any other suitable biocompatible material such as medical grade, biocompatible PTFE, polyethylene, silastic, neoprene, polypropylene, or polyurethane.

Figure 10:
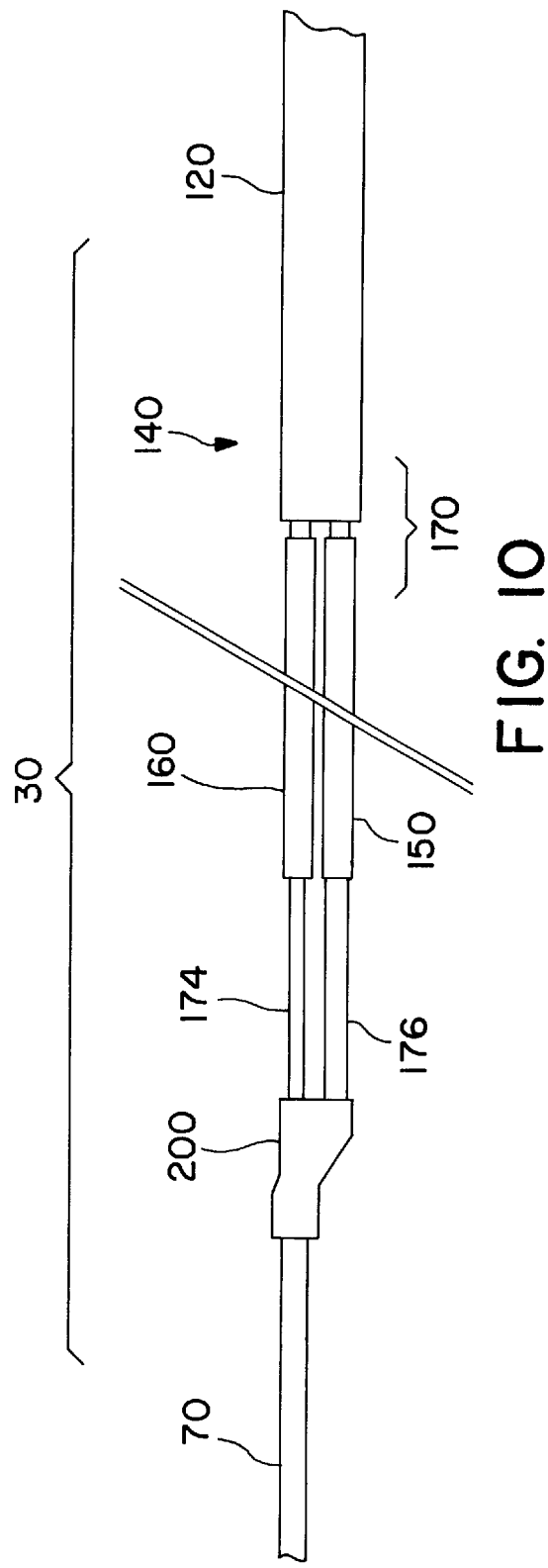
FIG. 10 shows an enlarged side view of a portion of a preferred embodiment of the present invention.

FIG. 10 shows an enlarged side view of a portion of the proximal end of a lead of the present invention, where two conductors and their corresponding layers of insulation are separated from one another at junction 200, most preferably formed of heat shrink tubing.

Figure 11:
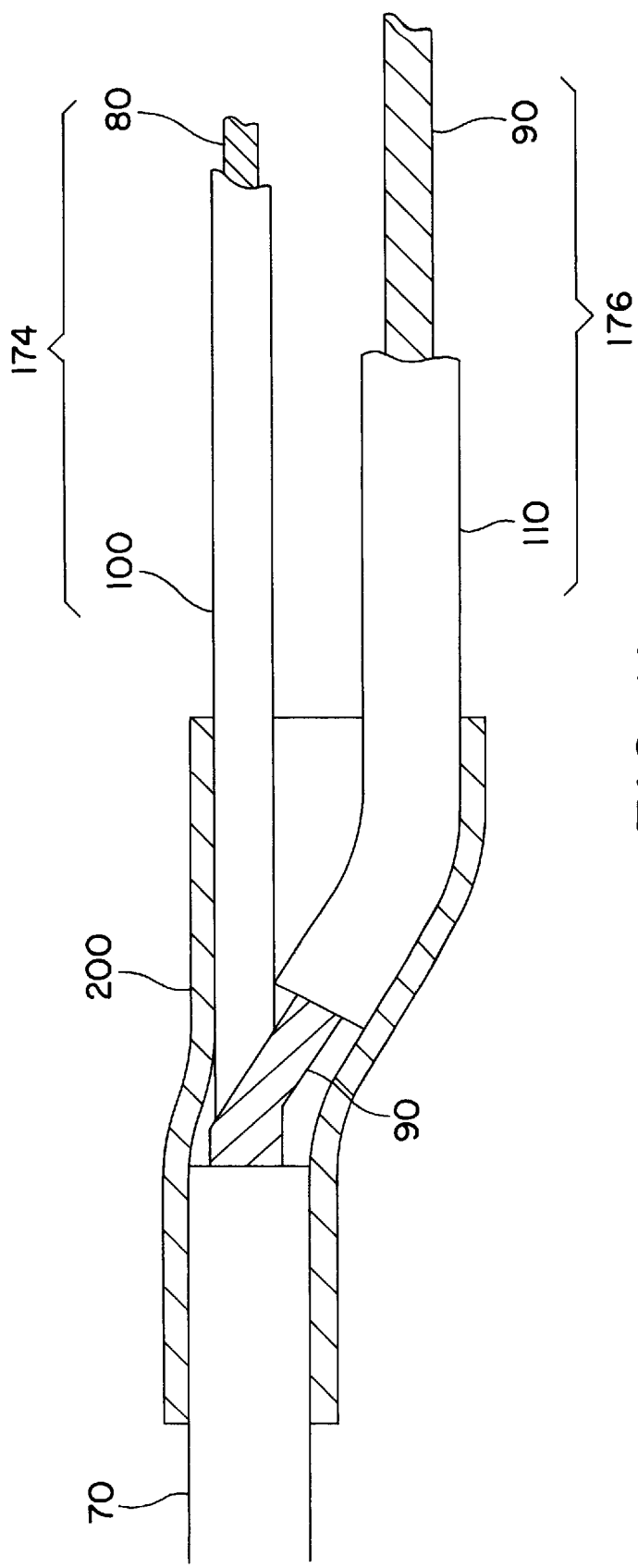
FIG. 11 shows an enlarged cross-sectional view of a portion of the proximal end of a preferred embodiment of the present invention.

FIG. 11 shows an enlarged cross-sectional view of junction 200, where coaxial conductor 70 is separated into two separate wires 174 and 176. First wire 174 comprises inner conductor 80 and inner insulation 100.

Second wire 176 comprises outer conductor 90 and outer insulation layer 110.

Figure 12:
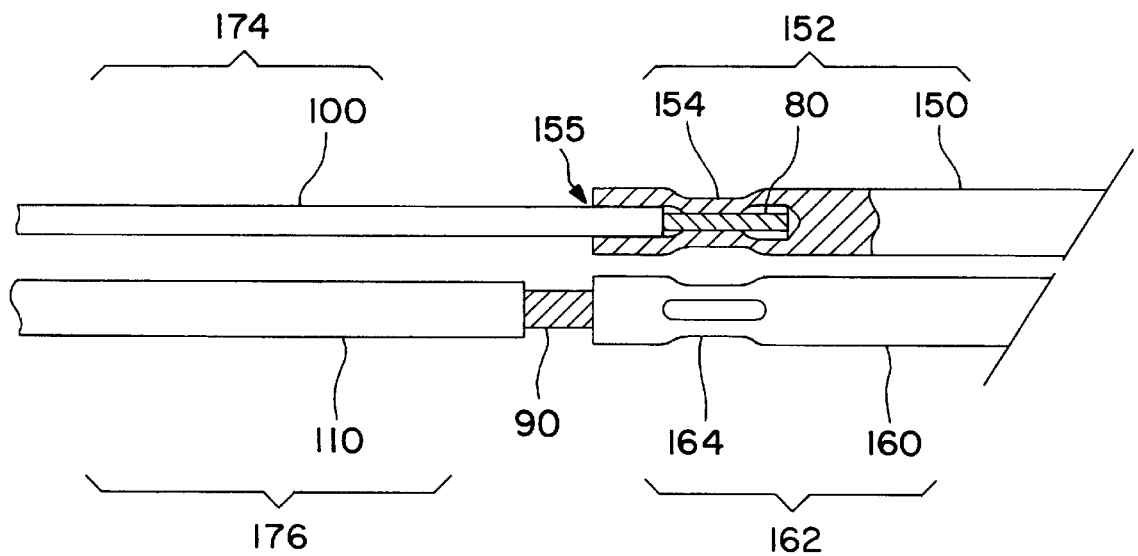
FIG. 12 shows an enlarged cross-sectional and side view of a portion of the proximal end of a preferred embodiment of the present invention.

At a distance proximal from junction 200 wires 174 and 176 are connected electrically and mechanically to connectors 150 and 160. As shown in FIG. 12, this is most preferably accomplished by stripping an appropriate length of overlying insulation away from the proximal ends of wires 174 and 176, compressing distal ends 152 and 162 of connectors 150 and 160 along vertical axes, inserting the bare wire ends into recesses 155 and 165, and crimping the wires in place to form crimps 154 and 164.

Figure 13:
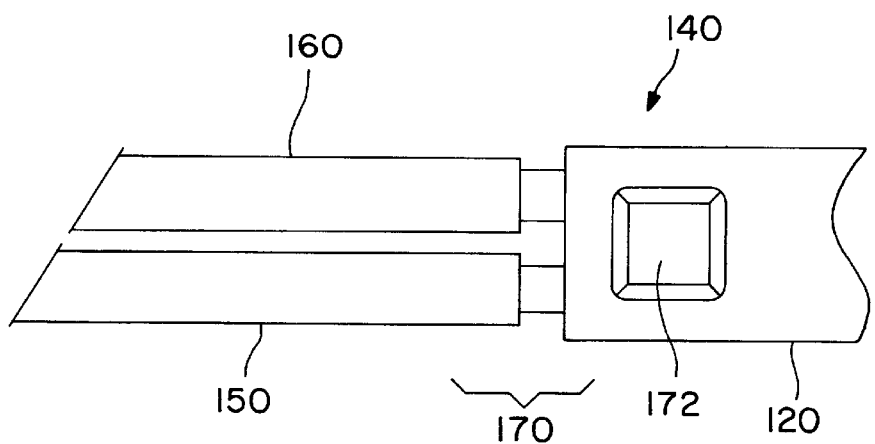
FIG. 13 shows an enlarged side view of a preferred embodiment of the weakened zone of the present invention.

FIG. 13 shows an enlarged side view of a preferred embodiment of weakened zone 170 of the present invention. Weakened zone 170 is shown being disposed between connectors 150 and 160 and needle 120. Crimp 172 compressionally holds pins 151 and 161 in blunt end 140 of needle 120.

The procedure for implanting lead 10 in the heart may be outlined briefly as follows. Fine curved needle 190 at distal end 20 of lead 10 is passed through the ventricular myocardium or epicardium. Affixation coil 60 and electrodes 40 and 50 are pulled through the heart tissue penetrated by needle 190 until the electrodes are located suitably within the myocardium or epicardium, and affixation coil 60 anchors electrodes 40 and 50 to the heart. Needle 190 and the portion of monofilament 180 extending from the heart are clipped off with a scissors, leaving the remainder of lead 10 extending from the heart. Chest needle 120 then pierces the patient's thorax, and is broken at weakened zone 170 to permit connectors 150 and 160 to be connected to an external sensing, monitoring, pacing or defibrillating device. When it is time to remove the lead, the surgeon simply carefully pulls the lead and withdraws it from the patient's heart and chest. Affixation coil 60 is flexible enough to allow the heart wire to be gently pulled from the myocardium or epicardium without damaging the myocardium.

Figure 14:
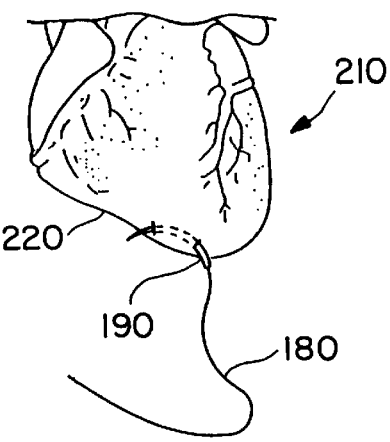
FIG. 14 shows a curved needle in a preferred embodiment of the present invention being inserted into the ventricular myocardium.

FIG. 14 shows curved needle 190 in a preferred embodiment of the present invention being inserted through epicardium 230 of ventricle 220 and into myocardium 240 of heart 210 preparatory to drawing bipolar lead 10 into myocardium 240 or epicardium 230.

Figure 15:
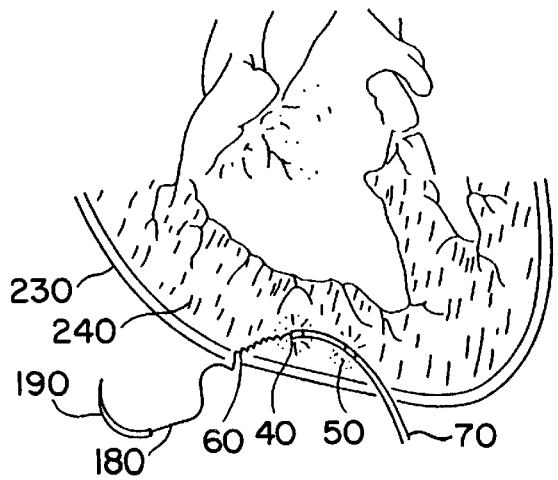
FIG. 15 shows a preferred embodiment of the present invention where both electrodes are positioned within the ventricular myocardium.
Figure 16:
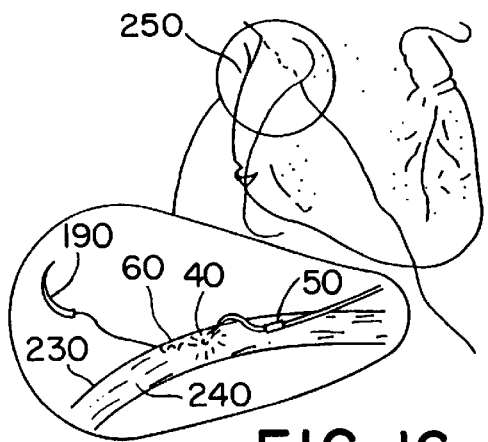
FIG. 16 shows a preferred embodiment of the present invention where the curved needle has pierced the atrial myocardium twice.

FIG. 15 shows a preferred embodiment of the present invention where electrodes 40 and 50 are positioned within ventricle 220 in myocardium 240 or epicardium 230. Optional affixation coil 60 prevents distal end 20 of lead 10 from FIG. 16 shows lead 10 positioned within myocardium 240 and epicardium 230 of atrium 250, where affixation coil 60 and electrodes 40 and 50 are positioned within myocardium 240 or epicardium 230. For atrial implantations the positioning of lead 10 shown in FIG. 16 may be preferred, where the surgeon pierces the atrium twice with curved needle 190, and a portion of lead 10 is positioned above heart 210. The lead positioning shown in FIG. 16 may be preferred as a means of preventing accidental penetration of the myocardium since the wall of atrium 250 is much thinner than that of ventricle 220.

Figure 17:
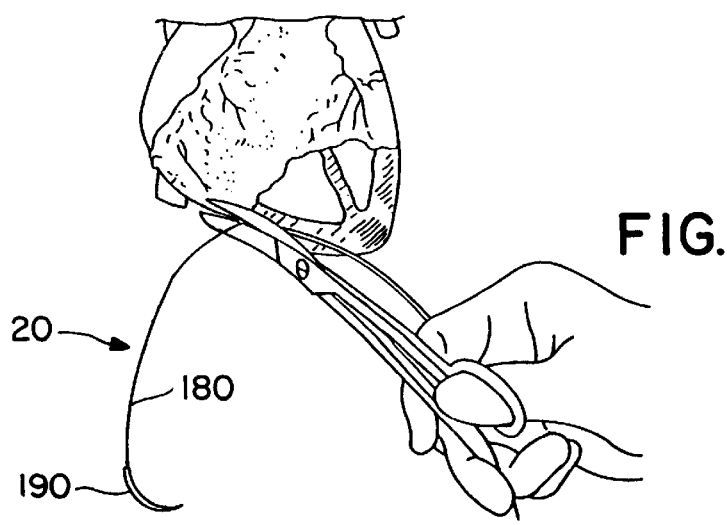
FIG. 17 shows removal of the curved needle from a heart wire of the present invention.

FIG. 17 shows the step in the implantation procedure where the surgeon cuts strand 180 at the exterior surface of the heart wall, leaving affixation coil 60 and electrodes 40 and 50 embedded in myocardium 240 or epicardium 230.

The temporary leads of the present invention shown in FIGS. 18 through 26 are generally intended to be used for temporary atrial or ventricular pacing and sensing, where the leads are implanted in a patient's myocardium for seven days or less. The temporary leads of FIGS. 18 through 26 should also be supplied in sterile condition and used a single time only before disposal.

As used herein and in respect of the embodiment of the present invention shown in FIGS. 18 through 26, the term "distal electrode 40" or "bare wire 41" means that portion of wire 40 having at least a portion of overlying electrical insulation 100 removed therefrom to expose a bare wire thereunder. As used herein and in respect of the embodiment of the present invention shown in FIGS. 18 through 26, the term "wire 40" means those portions of wire 40 that are covered by electrical insulation, do not function as an electrode, and form or are disposed near the distal end of first conductor 80.

Distal electrode 40 is mechanically and electrically connected by first conductor 80 to first connector 150 at the proximal end of lead 10, which, in turn, is mechanically connected to blunt end 140 of needle 120 by weakened zone 170. Most preferably, distal electrode 40 ranges between about 2 mm and about 10 mm in length, has a surface area ranging between about 1 and about 8 mm$^2$, and is formed of bare wire 41 extending between the distal end of insulation 100 and curved needle 190. The electrical wire disposed in first conductor 80 most preferably has an electrical resistance of about 20 ohms.

As used herein and in respect of the embodiment of the present invention shown in FIGS. 18 through 26, the term "proximal electrode 50" or "bare wire 51" means that portion of wire 50 having at least a portion of overlying electrical insulation 110 removed therefrom to expose a bare wire thereunder. As used herein and in respect of the embodiment of the present invention shown in FIGS. 18 through 26, the term "wire 50" means those portions of wire 50 that are covered by electrical insulation, do not function as an electrode, and form or are disposed near the distal end of second conductor 90.

In the embodiments of the present invention shown in FIGS. 18 through 26, proximal electrode 50 is mechanically and electrically connected by second conductor 90 to second connector 160 at the proximal end of lead 10, which is also, in turn, mechanically connected to blunt end 140 of needle 120 by weakened zone 170. It is preferred that proximal electrode 50 range between about 1 mm and about 12 mm in length, have a surface area ranging between about 1 and about 8 mm$^2$, be formed of bare wire 51, and be spaced proximally from the proximal-most portion of distal electrode 40 by a distance ranging between about 2 mm and about 10 mm. The electrical wire disposed in second conductor 90 most preferably has an electrical resistance of about 20 ohms. The particular dimensions selected for electrode length, electrode surface area and inter-electrode spacing depend in part upon the type and particular design features of the lead being considered (e.g., lamp-cord or co-axial).

In FIGS. 18 through 26, electrodes 40 and 50 are preferably formed of medical grade stainless steel suitable for temporary applications, and are preferably spaced a predetermined distance apart known to optimize the delivery of pacing pulses or the detection and sensing of cardiac electrical signals. In the embodiment of the present invention shown in FIGS. 18 through 26, insulation 110 or 100 may be removed to expose bare wire 51 or 41 in one of several ways. For example, insulation 100 or 110 may be removed by using a sharp scalpel to cut and remove insulation 100 or 100 away from wire 40 or 50. Alternatively, insulation 100 or 110 may be removed by positioning the appropriate portion of lead body 70 near a rotating brush operating at high speeds, the brush comprising polymeric strands which strip away the overlying insulation to expose bare wires 41 or 51. A soldering tip may also be employed to melt insulation 100 and 110 to expose bare wires 41 and 51. Still other methods of removing electrical insulation, such as using a wire stripper, may be employed to form electrodes 40 and 50.

Each of wires 40 and 50 most preferably comprises a plurality of twisted, braided or stranded medical grade wires formed from SST 316L, SST 304 or any other suitable, biocompatible metal. Each of wires 40 and 50 may also be formed of a single wire or up to 60 or more individual wires. In a preferred embodiment of the present invention, each of wires 40 and 50 is formed of 19 individual SST 316L wires stranded together, where each individual wire has a diameter of about 0.02 mm. Diameters of the wire or individual wires forming each of wires 40 and 50 most preferably range between about 0.01 mm and about 0.20 mm, depending on the number of wires employed to form each of wires 40 or 50. The preferred overall diameter of each of bare wires 40 and 50 is about 0.22 mm. Other diameters of wires 40 and 50 may be employed, and most preferably range between about 0.10 mm and about 0.60 mm. Other individual wire diameters and overall diameters of bare wires 40 and 50 may also be employed in the present invention. A preferred source of wire is Axon, S.A. of Montmireil, France. In preferred embodiments of the present invention, wires 40 and 50 have electrical resistances of about 20 ohms each.

In the embodiments of the present invention shown in FIGS. 18 through 26, lead body 70 may be formed of two conductors disposed side by side and having different colors such as yellow and purple to ease identification of the respective conductors by a user. So-called twin-conductor "lamp cord" or "zip-cord" is preferred for lead body 70 in this application. Lead body 70 may also comprise any pair of suitable flexible electrical conductors, such as coaxial conductors. For example, lead body 70 may comprise a coaxial pair of inner and outer electrical conductors, where the conductors are formed of helically wound strands of multifilament or twisted stainless steel. Lead body 70 most preferably comprises conductors that provide a high degree of flexibility, superior mechanical and electrical properties, and no or substantially no bending moment (more about which we say below).

In the embodiments of the present invention shown in FIGS. 18 through 26, needle 120, most preferably of the atraumatic type, is a chest needle for piercing the thorax, and has pointed end 130 and blunt end 140. Needle 120 is preferably substantially straight between pointed end 130 and blunt end 140. Pointed end 130 has a cutting edge designed for piercing the thoracic wall of the patient. Blunt end 140 attaches breakingly, snappingly, crimpingly, compressionally, adhesively, glueingly, elastically, slidingly or in otherwise suitable connecting yet separable fashion to the proximal ends of connectors 150 and 160. Weakened or pull-apart zone 170 separates the proximal ends of connectors 150 and 160 from blunt end 140. Connectors 150 and 160 most preferably form cylindrically shaped pin connectors having circular cross-sections upon being separated from blunt end 140. Other structural configurations of connectors 150 and 160 fall within the scope of the present invention and include, but are not limited to, pin-shaped connectors having rectangular or square cross-sections, reed-shaped connectors, and flexible connectors.

In the embodiments of the present invention shown in FIGS. 18 through 26, lead 10 includes curved needle 190 for piercing the myocardium or epicardium preparatory to drawing the heart wire 10 and its electrodes within the myocardium or epicardium. The proximal end of curved needle 190 is connected to strand 183.

The embodiments of the present invention shown in FIGS. 18 through 26 provide the advantages of requiring fewer components and manufacturing steps than are required in at least some of the other embodiments of the medical electrical leads shown and described in the specification hereof. For example, the embodiments of the present invention shown in FIGS. 18 through 26 require no discrete ring electrode components and no additional steps for attaching discrete electrodes to lead body 10.

Figure 18:
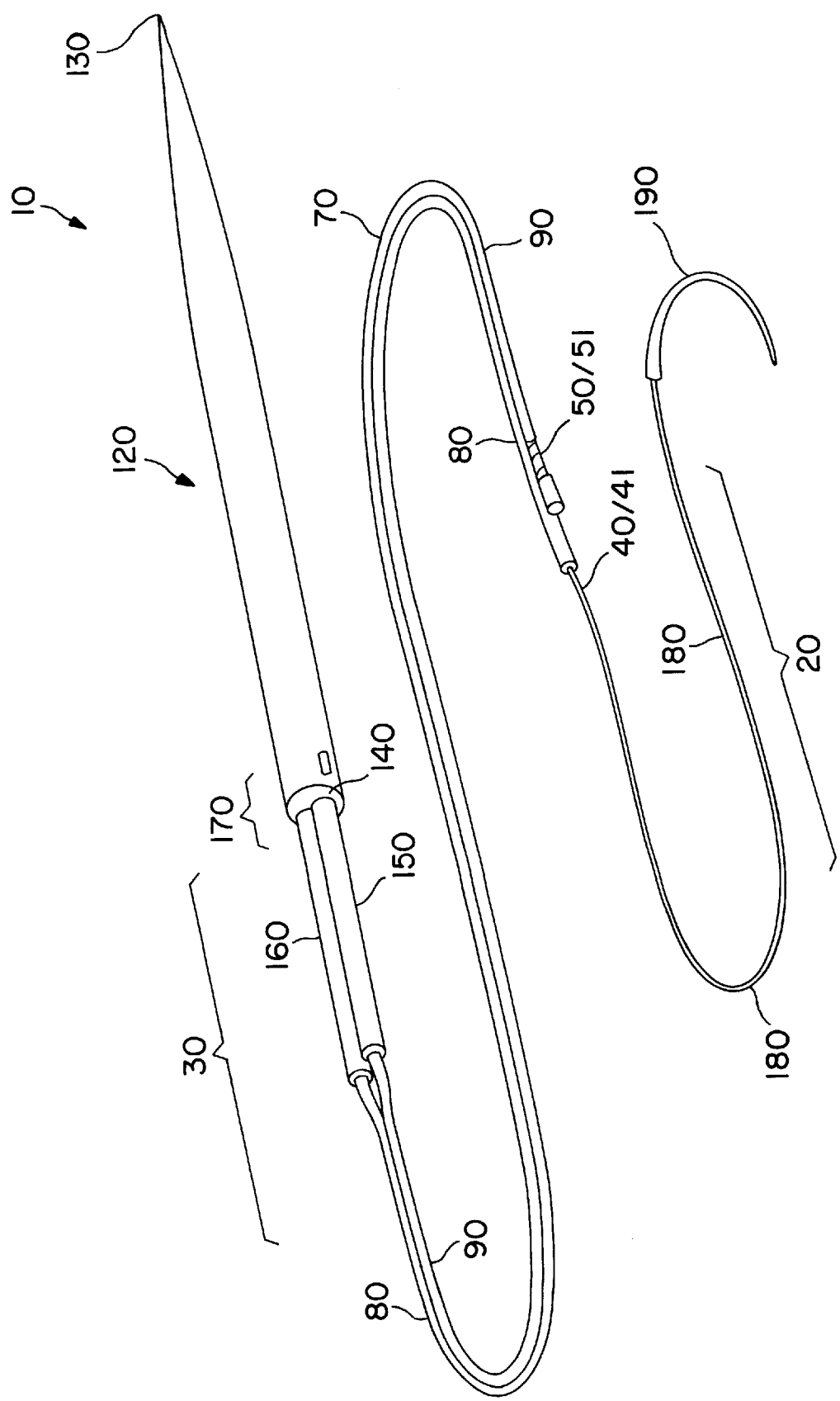
FIG. 18 shows a perspective view of one embodiment of a lead of the present invention.
Figure 19:
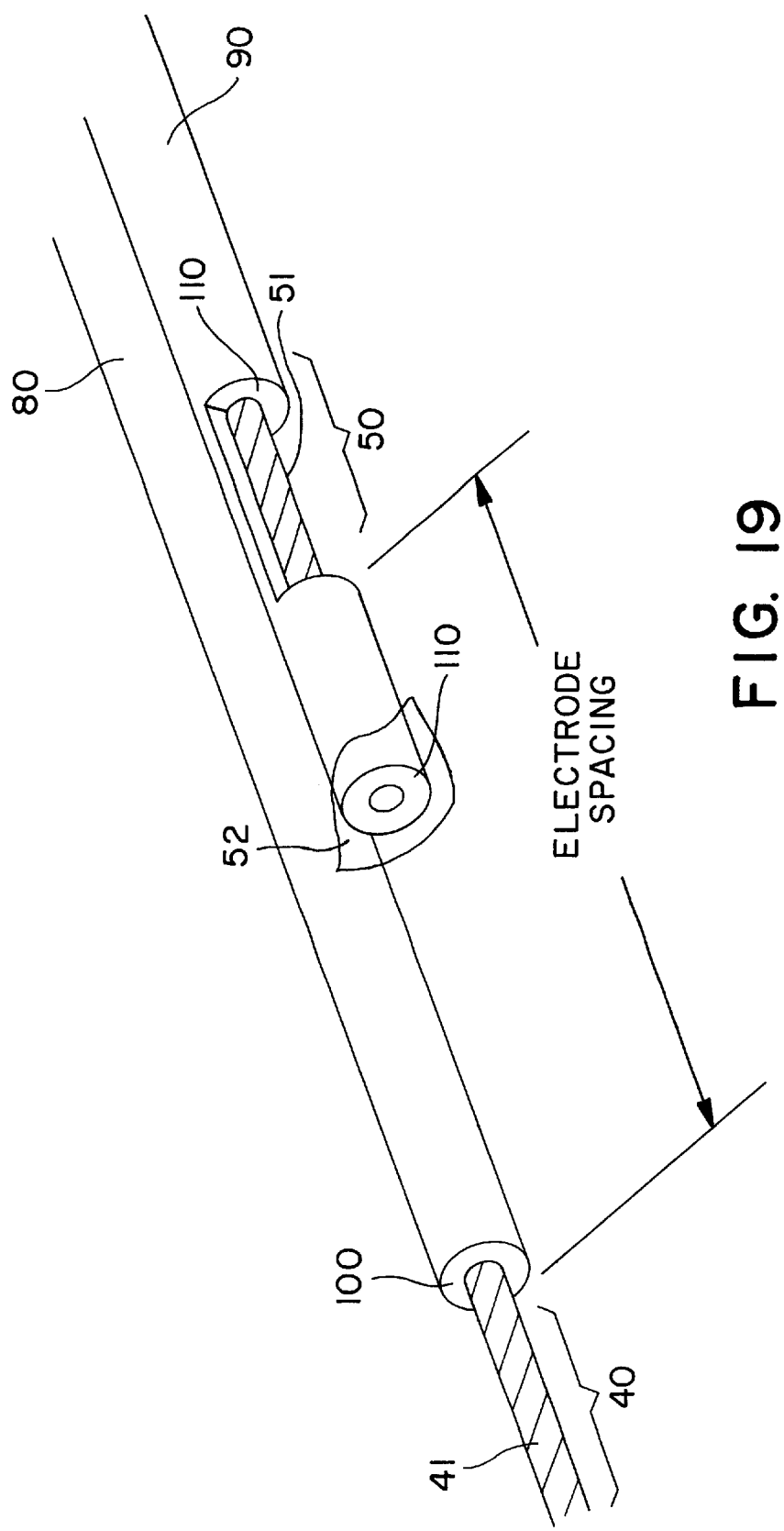
FIG. 19 shows an enlarged perspective view of a portion of the distal end of the lead of FIG. 18.
Figure 20A:
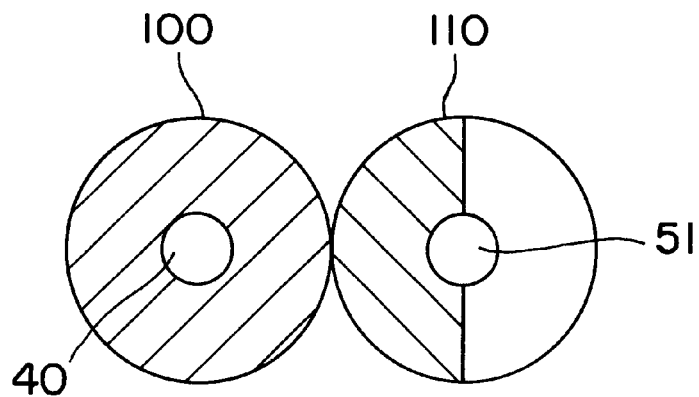
FIGS. 20(a) through 20(c) show cross-sectional views taken near the distal ends in the region of the proximal electrode for various embodiments of the present invention.
Figure 20B:
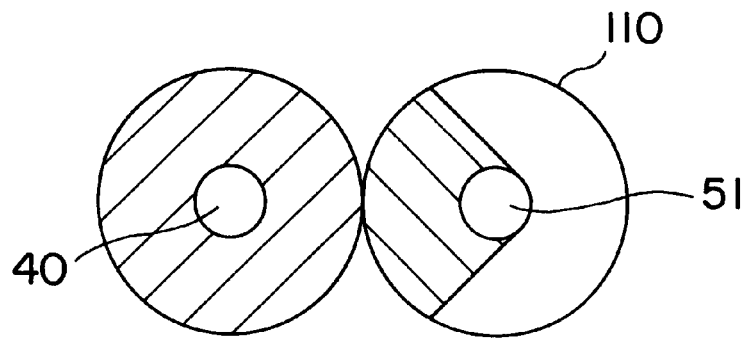
Figure 20C:
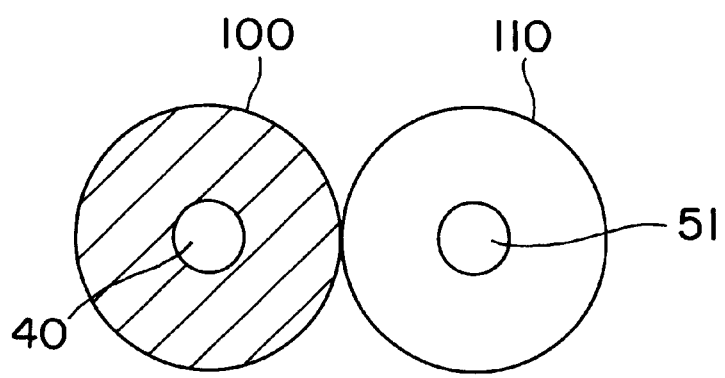

FIG. 18 shows a perspective view of a preferred low-cost embodiment of the present invention designed specifically for pacing and sensing applications. FIG. 19 shows an enlarged view of lead 10 in the proximity of proximal electrode 50 and distal electrode 40. In FIGS. 18 and 19, heart lead or wire 10 has distal end 20 and proximal end 30, and most preferably comprises needle 120, connectors 150 and 160, weakened zone 170, lead body 70 comprising lamp cord conductors 80 and 90, proximal electrode 50 formed of bare wire 51 exposed by removing overlying electrical insulation from the distal end of second conductor 90, distal electrode 40 formed of bare wire 41 exposed by removing overlying electrical insulation from the distal end of first conductor 80, and curved atraumatic needle 190. Proximal electrode 50 and distal electrode 40 may optionally be attached to the myocardium using sutures.

In the embodiment of the present invention shown in FIGS. 18 and 19, the distal end of second conductor 90 may be covered with UV adhesive joint 52 or shrink tube joint 53 to promote ease of insertion of lead 10 through the myocardium during surgery. Proximal electrode 50 or bare wire 51 may comprise a single wire or a plurality of individual wires stranded, twisted or braided together, wherein at least a portion of electrical insulation 110 covering bare wire 51 is removed.

In a preferred embodiment of the present invention, proximal electrode 50 is about 15 mm long, and is formed by bare wire 51. The distal end of second conductor 90 is most preferably secured to electrical insulation 100 and 110 by UV adhesive to form adhesive joint 52 or a heat shrink tube joint. Alternatively, suitable biocompatible glue or tape may affix or cover the distal end of second conductor 90.

FIGS. 20(*a*) through 20(*c*) show cross-sectional views of various embodiments of leads of the present invention similar to those shown in FIGS. 18 and 19 in the region of proximal electrodes 50 thereof. In FIG. 20(*a*), a cross-sectional view is shown of lead 10 where bare wire 51 forming electrode 50 has insulation 110 disposed about roughly half its circumference. In FIG. 20(*b*), a cross-sectional view is shown of lead 10 where bare wire 51 forming electrode 50 has insulation 110 disposed about less than half its circumference. In FIG. 20(*c*), a cross-sectional view is shown of lead 10 where bare wire 51 forming electrode 50 has insulation 110 disposed about none of its circumference.

Figure 21:
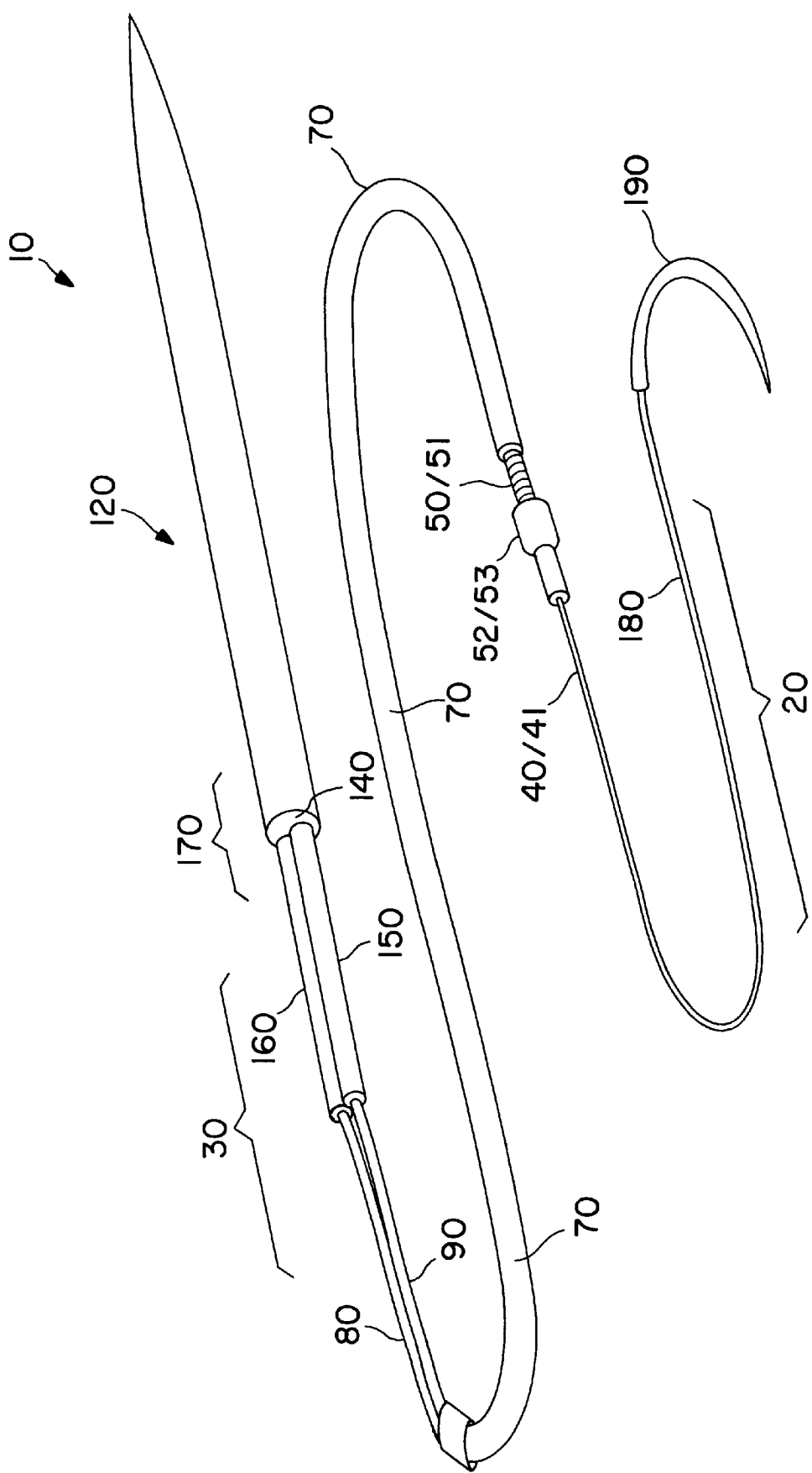
FIG. 21 shows a perspective view of another embodiment of a lead of the present invention.

FIG. 21 shows a perspective view of another preferred low-cost co-axial embodiment of the present invention designed specifically for pacing and sensing applications. FIGS. 22(*a*), 22(*b*), 23(*a*) and 23(*b*) show enlarged views of different embodiments of lead 10 of FIG. 21 in the region of proximal electrode 50 and distal electrode 40.

In FIGS. 21, 22(*a*), 22(*b*), 23(*a*) and 23(*b*), heart lead or wire 10 has distal end 20 and proximal end 30, and most preferably comprises needle 120, connectors 150 and 160, weakened zone 170, lead body 70 comprising co-axial conductors 80 and 90, proximal electrode 50 formed of bare wire 51 exposed by removing overlying electrical insulation from the distal end of second conductor 90, distal electrode 40 formed of bare wire 41 exposed by removing overlying electrical insulation from the distal end of first conductor 80, and curved atraumatic needle 190. Proximal electrode 50 and distal electrode 40 may optionally be attached to the myocardium using sutures. Adhesive joints 42 and 52 shown in FIGS. 22(*a*) and 22(*b*) promote ease of insertion and retraction of lead body 10 in and from myocardium 240 during implantation and explantation. Heat shrink joints 43 and 53 shown in FIGS. 23(*a*) and 23(*b*) likewise promote ease of insertion and retraction of lead body 10 in and from myocardium 240 during implantation and explantation, and also may have the advantage of being easier to form and dispose on lead 10 than adhesive joints.

When adhesive is employed to form adhesive joints 42 or 52 shown in the Figures, it is preferred that the adhesive be a POM (polyoxymethylene) UV-cured adhesive obtained from Dymax Corporation of Torrington, Conn. Adhesive joints 42 and 52 formed of such adhesive should be subjected to sufficiently intense UV radiation for a sufficient period of time to permit the adhesive to cure properly. A NOVACURETM UV Radiation Curing Instrument obtained from Efos, Inc. of Williamsville, N.Y. is most preferably employed in the UV-curing step. The adhesive is most preferably cured at room temperature in such an instrument set to deliver 2 20,000 mW/cm for between about 5 and about 10 seconds. When required, the adhesive forming adhesive joints 42 and 52 should be reworked after curing.

In an alternative embodiment of the present invention, the distal end of bare wire 51 is secured to first conductor 80 by biocompatible heat shrink tubing, as shown in FIG. 23(a). In another embodiment of the present invention, the distal end of insulation 110 is secured to bare wire 41 and insulation 100 by biocompatible heat shrink tubing, as shown in FIG. 23(b). Use of heat shrink tubing may result in an abrupt change in diameter occurring at locations where it is employed. Such abrupt changes in diameter may be avoided by tapering the edges or end portions of the heat shrink tubing, either before or after fitting to lead 10, or by selecting suitable thin-walled heat shrink tubing. Heat shrink tubing typically must be heated and set at relatively high temperatures (greater than about 120 degrees C) for periods of time that typically exceed the 5–10 seconds required to cure UV-cured adhesive. A preferred material for heat shrink tubing 43 or 53 is low density, biocompatible, medical grade polyethylene or polyolefin manufactured by Extrumed, Inc. of Orange, Calif., with titanium dioxide colorant conforming to ASTM D6398 and ASTM D876, and having expanded inner diameters ranging between about 0.054 inches and about 0.030 inches.

Additionally, heat shrink tubing may be employed to secure the distal end of second conductor 90 to first conductor 80, to cover the distal end of insulation 100 near bare wire 41, or may be formed of electrically conductive heat shrink tubing formed by mixing an appropriate polymer with sufficient quantities of electrically conductive particles or granules of stainless steel, carbon, platinum or platinum oxide, and polymerizing the resulting mixture. Other suitable, biocompatible electrically conductive materials might also be employed in such embodiments of the present invention. In less preferred embodiments of the present invention, the distal end of second conductor 90 may be secured to first conductor 80 by biocompatible polyurethane, biocompatible two-compound adhesives such as epoxy, biocompatible tape or other suitable means.

Figures 24A, 24B:
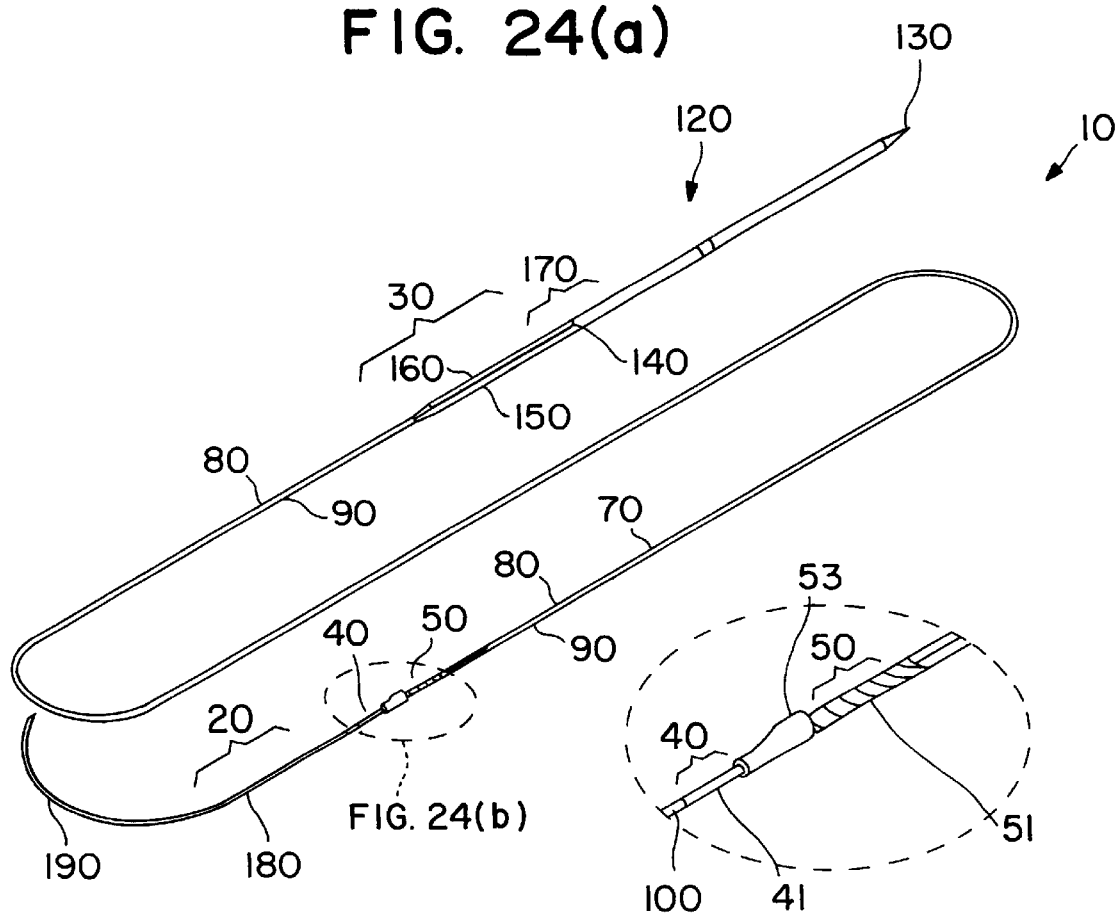
FIGS. 24(a) and 24(b) show a perspective view of yet another embodiment of a lead of the present invention.

FIG. 24(a) shows another embodiment of the lead of the present invention, where lead body 70 is a lamp-cord formed of two side-by-side conductors 80 and 90. FIG. 24(b) shows an enlarged view of lead 10 of FIG. 24(a) in the region of proximal and distal electrodes 50 and 40. Note that proximal electrode 50 is formed of twisted bare wire 51. Insulation 100 disposed distally of bare wire 41 is optional, and is preferably not present between distal electrode 40 and needle 190 to avoid having portions of insulation 100 tear off or separate from lead 10, only to be left in myocardium 240 of a patient when lead 10 is retracted therefrom. In lead 10 of FIGS. 24(a) and 24(b), insulation 100 and 110 in the vicinity of bare wires 41 and 51 is most preferably removed using the aforementioned brushing technique.

Preferred specifications for lead 10 of FIGS. 24(a) and 24(b) include the following: (a) 0.008 inch diameter stranded wire for each of electrodes 40 and 50; (b) distal electrode 40 length of 0.30 inches; (c) proximal electrode 50 length of 0.75 inches; (d) distal electrode surface area of 0.05 inches squared; (e) proximal electrode surface area of 0.19 inches squared; (f) inter-electrode spacing of 0.30 inches; (g) proximal electrode twisted about insulator 100; (h) electrodes, lead connectors, needles and conductors formed of surgical grade stainless steel.

Insulation 100 and insulation 110 of conductors 80 and 90, respectively, in FIGS. 24(a) and 24(b) are most preferably colored yellow and purple, respectively, to permit easy, rapid identification and differentiation by a physician. In the embodiment of the present invention shown in FIGS. 24(a) and 24(b), it is preferred that distal electrode 40 be employed as the cathode, and that proximal electrode 50 be employed as the anode, when lead 10 is implanted in myocardium 240. It is to be understood, however, that the anode and cathode may be interchanged in any of the embodiments of lead 10 of the present invention shown herein.

FIGS. 25 and 26 illustrate yet other embodiments and corresponding methods of the present invention, where electrodes 40 and 50 are positioned in myocardium 240 or epicardium 230. The atrium may be pierced just once when the embodiments of the present invention shown in FIGS. 25 and 26 are employed by, for example, positioning proximal electrode 50 (operating most preferably as an anode) on or near the surface of heart 210 and positioning distal electrode 40 (operating most preferably as a cathode) in epicardium 230 or myocardium 240 of heart 210. FIG. 25 shows a preferred embodiment and corresponding method of the present invention similar to those illustrated in FIGS. 18, 19 and 20(a) through 20(c), where both electrodes are positioned within the ventricular myocardium. FIG. 26 shows a preferred embodiment and corresponding method of the present invention similar to those illustrated in FIGS. 21, 22(a), 22(b), 23(a) and 23(b), where both electrodes are positioned within the ventricular myocardium.

Note that the co-axial embodiments of lead 10 shown in FIGS. 21, 22(a), 22(b), FIGS. 23(a), 23(b) and FIG. 26 are preferred embodiments of the present invention because proximal electrodes 50 thereof may be made shorter than their counterparts in lamp-cord type leads. This result obtains, at least in part, because in co-axial lead configurations of the present invention, proximal electrode 50 has increased surface area relative to a proximal electrode in a lamp-cord type of lead 10, and therefore may be made shorter in length. This, in turn, means that the electrode portion of lead 10 may be made more compact or shorter in length, and therefore may be inserted in myocardium 240 or epicardium 230 over shorter tunnel lengths thereof. The co-axial lead shortened electrode geometry permits a physician to implant lead 10 at a shallower depth in heart 210 than is generally possible using a lamp-cord type of lead 10.

Additionally, owing to the structural uniformity of their cross-sections, co-axial embodiments of the present invention have no or substantially no bending moments associated therewith. In contrast, lamp-cord type leads of the present invention do have bending moments associated therewith. Those bending moments arise from the structurally non-uniform cross-sections of lamp-cord type leads, and may cause the lead to shift or move in the myocardium or epicardium following implantation. Finally, co-axial leads of the present invention have an advantage compared to lamp-cord type leads in the respect that insulation 100 and 110 is substantially less prone to peel away from the underlying wire in co-axial leads than in lamp-cord type leads during lead implantation or removal. (Undesired peeling away of insulation 100 or 110 from the underlying wire may cause lead insertion or retraction forces to increase substantially.)

Although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

For example, the Figures show Keith-type needles, but any needle having suitably shaped and configured pointed and blunt ends and a suitable shank portion may be used. The needle need not be formed of stainless steel or an electrically conductive material, but may be formed of medical grade plastic, polymers or any other suitable material. Moreover, there is no requirement that the needle of the present invention be straight, substantially straight or solid in cross-section. Indeed, the needle of the present invention may be curved or hollow. Finally, the needle of the present invention need not have a pointed end because in some cases the needle may be withdrawn from a patient's body through an existing natural or surgically made orifice, hole or opening.

Since the connectors of the present invention are required to be in electrical contact with the conductors, the conductors are preferably attached to the distal ends of the connectors by a combination of compressing, inserting and crimping steps. Other methods of electrically conductive attachment such as brazing, soldering or welding may of course be utilized. The connectors of the present invention are not limited to pin connectors, but include any plurality of connectors having suitable configurations for attachment to the blunt end. The proximal ends of the connectors need not be removed from the needle by manual means only. Specially configured tools may be used to break or pull the connectors free of the needle.

The present invention is not limited to embodiments where the weakened zone breaks upon the application of sufficient bending moment thereto, or where the proximal ends of the connectors attach directly to the blunt end. The weakened zone may be formed of connectors whose distal ends attach glueingly, vaccuumingly, elastically or otherwise to the blunt end, or whose distal ends pull out of the blunt end upon sufficient pulling force being applied thereto. The weakened zone may further comprise an intermediate member disposed between the proximal ends of the connectors and the blunt end that may not be electrically conductive. For example, an intermediate member might be formed of plastic and be configured to break upon the application of an appropriate bending moment. The resulting separated connectors would then have non-conductive plastic portions disposed on their proximal ends, but those portions would not preclude effective electrical and mechanical connection between the connectors and an external electrical apparatus. Alternatively, the weakened zone might be formed, at least partially, of medical grade heat shrink tubing.

Furthermore, the present invention is not limited to embodiments where all electrodes are attached to the same lead body, where one electrode must necessarily be disposed proximally or distally of the other electrode or electrodes, or where the electrodes are crimpingly attached to the conductors. For example, an electrode of the present invention may be formed by merely stripping away insulation overlying bare wire at a suitable location, by attaching a clip to bare wire, or by heat shrinking electrically conductive heat shrink over selected portions of bare wire. Nor is the present invention limited to embodiments where the electrodes are introduced surgically with the aid of a curved needle through or into cardiac or other tissue. The present invention includes within its scope embodiments where the electrodes may be located on the surface of the heart, inside the atrium or ventricle, or on or in the endocardium.

The scope of the present invention is not limited to pacing, monitoring or sensing applications, but extends to neural, defibrillation, cardiac mapping, abdominal stimulation, and other medical and medical device applications and methods. The scope of the present invention is not limited to applications where a human organ or plurality of organs is sensed, monitored, paced, or defibrillated, but includes similar applications in animals.

In the claims, means-plus function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The present invention further includes within its scope methods of implanting, using and making the leads described hereinabove. For example, the invention includes a method for implanting a temporary lead having distal and proximal ends, the lead being suitable for pacing, sensing, monitoring, or defibrillating at least a portion of a human or animal organ, the method comprising the steps of: (a) positioning at least two electrodes in electrical contact with the portion of the organ, the electrodes being electrically connected to first and second electrical conductors, respectively, the conductors having proximal ends connected electrically to first and second connectors, respectively, the connectors being configured for attachment to an external electrical apparatus; (b) securing the electrodes to the portion of the organ; and (c) separating the connectors from a blunt end of a chest needle having distal and proximal ends, the blunt end being disposed at the distal end of the needle, by application of a sufficiently large bending moment to a weakened zone disposed between the blunt end and the connectors. The foregoing method may optionally include the steps of: (a) a first piercing step that precedes the positioning step, the first piercing step comprising the step of piercing the organ with a pointed end of a curved needle, the curved needle being attached to the distal end of the lead, or (b) a second piercing preceding the separating step, the second piercing step comprising the step of piercing the thorax of a patient with a pointed end of the chest needle, the pointed end being disposed at the proximal end of the chest needle, or (c) a connecting step following the separating step, the connecting step comprising the step of electrically connecting the connectors to an external electrical apparatus. Alternatively, the separating step may be accomplished by application of a sufficiently large pulling force to the weakened zone such that the connectors are separated from the blunt end.

The present invention also includes within its scope a method for making a temporary lead having distal and proximal ends, where the lead is suitable for pacing, sensing, monitoring, or defibrillating at least a portion of a human or animal organ. The method of making comprises the steps of:

(a) providing a lead body having distal and proximal ends and comprising at least first and second electrical conductors having proximal ends;

(b) forming at least first and second electrodes, the first and second electrodes being electrically connected to the first and second electrical conductors, respectively; (c) providing a needle having distal and proximal ends, the needle having a blunt end disposed at its distal end; (d) providing first and second connectors; (e) attaching the first and second connectors to the proximal ends of the first and second electrical conductors, respectively; (f) providing a weakened zone between the first and second electrical connectors and the blunt end, the connectors being separated from the blunt end by application of a sufficiently large bending moment to the weakened zone, the connectors being configured for attachment to an external electrical apparatus. Alternatively, the separating step may be accomplished by application of a sufficiently large pulling force to the weakened zone.

We claim:

1. A temporary medical lead having distal and proximal ends, the lead being suitable for pacing, sensing, monitoring, or defibrillating at least a portion of a human or animal organ, comprising:

(a) a lead body having distal and proximal ends and comprising at least first and second side-by-side lamp-cord electrical conductors having proximal and distal ends, the first and second electrical conductors being electrically insulated from one another, at least portions of the first and second conductors being covered by electrically insulative material, the first and second conductors being formed of one or a plurality of wires or stranded wires;

(b) a distal electrode comprising at least one or a plurality of bare wires disposed at or near the distal end of the first conductor, the distal electrode having no electrical insulation material disposed thereover;

(c) a proximal electrode comprising at least one or a plurality of bare wires disposed at or near the distal end of the second conductor, the second conductor being shorter than the first conductor, the distal end of the second conductor being disposed proximally of the distal end of the first conductor, the proximal electrode having no electrical insulation material disposed thereover;

(d) at least one of biocompatible heat shrink tubing and biocompatible adhesive disposed at the distal end of the second conductor to thereby secure the second conductor to the first conductor and facilitate implantation and explantation of the lead from a mammalian heart;

(e) a needle having distal and proximal ends, the needle having a blunt end disposed at its distal end;

(f) at least first and second connectors, the first connector being attached to the proximal end of the first electrical conductor, the second connector being attached to the proximal end of the second electrical conductor, and (g) a weakened zone disposed between the first and second electrical connectors and the blunt end;

wherein the connectors may be separated from the blunt end by the application of one of a sufficiently large bending moment and a sufficiently large pulling force to the weakened zone, and the connectors are configured for attachment to an external electrical apparatus.

2. The temporary lead of claim 1, wherein electrical insulation material is disposed distally from the proximal electrode over the second conductor.

3. The temporary lead of claim 1, wherein no electrical insulation material is disposed distally from the distal electrode over the first conductor.

4. The temporary lead of claim 1, wherein the proximal electrode is an at least partially bare wire wound around the first conductor.

5. The temporary lead of claim 1, wherein the adhesive is one of a UV-cured adhesive and epoxy.

6. The temporary lead of claim 5, wherein the UV-cured adhesive is polymethylene UV-cured adhesive.

7. The temporary lead of claim 1, wherein the first and second conductors are formed of at least one of helically wound strands of multifilament stainless steel, twisted strands of multifilament stainless steel, single strands of stainless steel, and strands of electrically conductive polymeric material.

8. The temporary lead of claim 1, wherein the at least first and second electrical conductors are zip cord conductors.

9. The temporary lead of claim 1, wherein the distal and proximal electrodes are formed of medical grade stainless steel.

10. The temporary lead of claim 1, wherein the proximal electrode ranges between about 1 mm and about 12 mm in length.

11. The temporary lead of claim 1, wherein the distal electrode ranges between about 1 mm and about 10 mm in length.

12. The temporary lead of claim 1, wherein the proximal electrode has a surface area ranging between about 1 $mm^2$ and about 8 $mm^2$.

13. The temporary lead of claim 1, wherein the distal electrode has a surface area ranging between about 1 $mm^2$ and about 8 $mm^2$.

14. The temporary lead of claim 1, wherein at least one of biocompatible heat shrink tubing and biocompatible adhesive disposed at the distal end of the first conductor to facilitate implantation and explantation of the lead from a mammalian heart.

15. A temporary medical lead having distal and proximal ends, the lead being suitable for pacing, sensing, monitoring, or defibrillating at least a portion of a human or animal organ, comprising:

(a) a lead body having distal and proximal ends and comprising at least first inner and second outer co-axial electrical conductors having proximal and distal ends, the first and second electrical conductors being electrically insulated from one another, at least portions of the first and second conductors being covered by electrically insulative material, the first and second conductors being formed of one or a plurality of wires or stranded wires;

(b) a distal electrode comprising at least one or a plurality of bare wires disposed at or near the distal end of the first conductor, the distal electrode having no electrical insulation material disposed thereover;

(c) a proximal electrode comprising at least one or a plurality of bare wires disposed at or near the distal end of the second conductor, the second conductor being shorter than the first conductor, the distal end of the second conductor being disposed proximally of the distal end of the first conductor, the proximal electrode having no electrical insulation material disposed thereover;

(d) at least one of biocompatible heat shrink tubing and biocompatible adhesive disposed at the distal end of the second conductor to thereby secure the second conductor to the first conductor and facilitate implantation and explantation of the lead from a mammalian heart;

(e) a needle having distal and proximal ends, the needle having a blunt end disposed at its distal end;

(f) at least first and second connectors, the first connector being attached to the proximal end of the first electrical conductor, the second connector being attached to the proximal end of the second electrical conductor, and (g) a weakened zone disposed between the first and second electrical connectors and the blunt end;

wherein the connectors may be separated from the blunt end by the application of one of a sufficiently large bending moment and a sufficiently large pulling force to the weakened zone, and the connectors are configured for attachment to an external electrical apparatus.

16. The temporary lead of claim 15, wherein at least one of biocompatible heat shrink tubing and biocompatible adhesive disposed at the distal end of the second conductor to facilitate implantation and explantation of the lead from a mammalian heart.

17. The temporary lead of claim 15, wherein a layer of inner insulation separates and electrically insulates the first inner conductor from the second outer conductor, the inner insulation being formed from a material selected from the group consisting of fluorinated ethylene propylene (FEP), polytetrafluorethylene (PTFE), co-polymer polytetrafluorethylene, polyethylene, silastic, neoprene, polypropylene and polyurethane.

18. The temporary lead of claim 17, wherein the outer conductor is composed of between about 26 and 40 medical grade stainless steel strands or filaments wound helically over the layer of inner insulation.

19. The temporary lead of claim 17, wherein the inner conductor is composed of about 19 medical grade twisted, wound, or twisted and wound stainless steel filaments or strands.

20. The temporary lead of claim 15, wherein a layer of outer insulation is disposed over the outer surface of the second conductor, the outer insulation being electrically insulative and formed from a material selected from the group consisting of FEP, polyethylene, biocompatible PTFE, polyethylene, silastic, neoprene, polypropylene and polyurethane.

21. The temporary lead of claim 15, wherein a layer of outer insulation is disposed over the outer surface of the first conductor, the outer insulation being electrically insulative and formed from a material selected from the group consisting of FEP, polyethylene, biocompatible PTFE, polyethylene, silastic, neoprene, polypropylene and polyurethane.

22. The temporary lead of claim 15, wherein electrical insulation material is disposed distally from the proximal electrode over the second conductor.

23. The temporary lead of claim 15, wherein no electrical insulation material is disposed distally from the distal electrode over the first conductor.

24. The temporary lead of claim 15, wherein the proximal electrode is an at least partially bare wire wound around the first conductor.

25. The temporary lead of claim 15, wherein the adhesive is one of a UV-cured adhesive and epoxy.

26. The temporary lead of claim 25, wherein the UV-cured adhesive is polymethylene UV-cured adhesive.

27. The temporary lead of claim 15, wherein the first and second conductors are formed of at least one of helically wound strands of multifilament stainless steel, twisted strands of multifilament stainless steel, single strands of stainless steel, and strands of electrically conductive polymeric material.

28. The temporary lead of claim 15, wherein the distal and proximal electrodes are formed of medical grade stainless steel.

29. The temporary lead of claim 15, wherein the proximal electrode ranges between about 1 mm and about 12 mm in length.

30. The temporary lead of claim 15, wherein the distal electrode ranges between about 1 mm and about 10 mm in length.

31. The temporary lead of claim 15, wherein the proximal electrode has a surface area ranging between about 1 mm$^2$ and about 8 mm$^2$.

32. The temporary lead of claim 15, wherein the distal electrode has a surface area ranging between about 1 mm$^2$ and about 8 mm$^2$.

33. A temporary medical lead having distal and proximal ends, the lead being suitable for pacing, sensing, monitoring, or defibrillating at least a portion of a human or animal organ, comprising:

(a) a lead body having distal and proximal ends and comprising at least first and second side-by-side lampcord electrical conductors having proximal and distal ends, the first and second electrical conductors being electrically insulated from one another, at least portions of the first and second conductors being covered by electrically insulative material, the first and second conductors being formed of one or a plurality of wires or stranded wires;

(b) a distal electrode comprising at least one or a plurality of bare wires disposed at or near the distal end of the first conductor, the distal electrode having no electrical insulation material disposed thereover;

(c) a proximal electrode comprising at least one or a plurality of bare wires disposed at or near the distal end of the second conductor, the second conductor being shorter than the first conductor, the distal end of the second conductor being disposed proximally of the distal end of the first conductor, the proximal electrode having no electrical insulation material disposed thereover, and wherein electrical insulation material is disposed distally from the proximal electrode over the second conductor;

(d) at least one of biocompatible heat shrink tubing and biocompatible adhesive disposed at the distal end of the second conductor to thereby secure the second conductor to the first conductor and facilitate implantation and explantation of the lead from a mammalian heart;

(e) a needle having distal and proximal ends, the needle having a blunt end disposed at its distal end;

(f) at least first and second connectors, the first connector being attached to the proximal end of the first electrical conductor, the second connector being attached to the proximal end of the second electrical conductor, and (g) a weakened zone disposed between the first and second electrical connectors and the blunt end;

wherein the connectors may be separated from the blunt end by the application of one of a sufficiently large bending moment and a sufficiently large pulling force to the weakened zone, and the connectors are configured for attachment to an external electrical apparatus.

34. The temporary lead of claim 33, wherein electrical insulation material is disposed distally from the proximal electrode over the second conductor.

35. The temporary lead of claim 33, wherein no electrical insulation material is disposed distally from the distal electrode over the first conductor.

36. The temporary lead of claim 33, wherein the proximal electrode is an at least partially bare wire wound around the first conductor.

37. The temporary lead of claim 33, wherein the adhesive is one of a UV-cured adhesive and epoxy.

38. The temporary lead of claim 37, wherein the UV-cured adhesive is polymethylene UV-cured adhesive.

39. The temporary lead of claim 33, wherein the first and second conductors are formed of at least one of helically wound strands of multifilament stainless steel, twisted strands of multifilament stainless steel, single strands of stainless steel, and strands of electrically conductive polymeric material.

40. The temporary lead of claim 33, wherein the at least first and second electrical conductors are zip cord conductors.

41. The temporary lead of claim 33, wherein the distal and proximal electrodes are formed of medical grade stainless steel.

42. The temporary lead of claim 33, wherein the proximal electrode ranges between about 1 mm and about 12 mm in length.

43. The temporary lead of claim 33, wherein the distal electrode ranges between about 1 mm and about 10 mm in length.

44. The temporary lead of claim 33, wherein the proximal electrode has a surface area ranging between about 1 $mm^2$ and about 8 $mm^2$.

45. The temporary lead of claim 33, wherein the distal electrode has a surface area ranging between about 1 $mm^2$ and about 8 $mm^2$.

46. The temporary lead of claim 33, wherein at least one of biocompatible heat shrink tubing and biocompatible adhesive disposed at the distal end of the first conductor to facilitate implantation and explantation of the lead from a mammalian heart.

47. A temporary medical lead having distal and proximal ends, the lead being suitable for pacing, sensing, monitoring, or defibrillating at least a portion of a human or animal organ, comprising:
   (a) a lead body having distal and proximal ends and comprising at least first inner and second outer co-axial electrical conductors having proximal and distal ends, the first and second electrical conductors being electrically insulated from one another, at least portions of the first and second conductors being covered by electrically insulative material, the first and second conductors being formed of one or a plurality of wires or stranded wires;
   (b) a distal electrode comprising at least one or a plurality of bare wires disposed at or near the distal end of the first conductor, the distal electrode having no electrical insulation material disposed thereover;
   (c) a proximal electrode comprising at least one or a plurality of bare wires disposed at or near the distal end of the second conductor, the second conductor being shorter than the first conductor, the distal end of the second conductor being disposed proximally of the distal end of the first conductor, the proximal electrode having no electrical insulation material disposed thereover;
   (d) at least one of biocompatible heat shrink tubing and biocompatible adhesive disposed at the distal end of each of the first and the second conductor to thereby secure the second conductor to the first conductor and facilitate implantation and explantation of the lead from a mammalian heart;
   (e) a needle having distal and proximal ends, the needle having a blunt end disposed at its distal end;
   (f) at least first and second connectors, the first connector being attached to the proximal end of the first electrical conductor, the second connector being attached to the proximal end of the second electrical conductor, and
   (g) a weakened zone disposed between the first and second electrical connectors and the blunt end;
wherein the connectors may be separated from the blunt end by the application of one of a sufficiently large bending moment and a sufficiently large pulling force to the weakened zone, and the connectors are configured for attachment to an external electrical apparatus.

48. The temporary lead of claim 47, wherein a layer of inner insulation separates and electrically insulates the first inner conductor from the second outer conductor, the inner insulation being formed from a material selected from the group consisting of fluorinated ethylene propylene (FEP), polytetrafluorethylene (PTFE), co-polymer polytetrafluorethylene, polyethylene, silastic, neoprene, polypropylene and polyurethane.

49. The temporary lead of claim 47, wherein the outer conductor is composed of between about 26 and 40 medical grade stainless steel strands or filaments wound helically over the layer of inner insulation.

50. The temporary lead of claim 49, wherein the inner conductor is composed of about 19 medical grade twisted, wound, or twisted and wound stainless steel filaments or strands.

51. The temporary lead of claim 47, wherein a layer of outer insulation is disposed over the outer surface of the second conductor, the outer insulation being electrically insulative and formed from a material selected from the group consisting of FEP, polyethylene, biocompatible PTFE, polyethylene, silastic, neoprene, polypropylene and polyurethane.

52. The temporary lead of claim 47, wherein a layer of outer insulation is disposed over the outer surface of the first conductor, the outer insulation being electrically insulative and formed from a material selected from the group consisting of FEP, polyethylene, biocompatible PTFE, polyethylene, silastic, neoprene, polypropylene and polyurethane.

53. The temporary lead of claim 47, wherein electrical insulation material is disposed distally from the proximal electrode over the second conductor.

54. The temporary lead of claim 47, wherein no electrical insulation material is disposed distally from the distal electrode over the first conductor.

55. The temporary lead of claim 47, wherein the proximal electrode is an at least partially bare wire wound around the first conductor.

56. The temporary lead of claim 47, wherein the adhesive is one of a UV-cured adhesive and epoxy.

57. The temporary lead of claim 56, wherein the UV-cured adhesive is polymethylene UV-cured adhesive.

58. The temporary lead of claim 47, wherein the first and second conductors are formed of at least one of helically wound strands of multifilament stainless steel, twisted strands of multifilament stainless steel, single strands of stainless steel, and strands of electrically conductive polymeric material.

59. The temporary lead of claim 47, wherein the distal and proximal electrodes are formed of medical grade stainless steel.

60. The temporary lead of claim 47, wherein the proximal electrode ranges between about 1 mm and about 12 mm in length.

61. The temporary lead of claim 47, wherein the distal electrode ranges between about 1 mm and about 10 mm in length.

62. The temporary lead of claim 47, wherein the proximal electrode has a surface area ranging between about 1 $mm^2$ and about 8 $mm^2$.

63. The temporary lead of claim 47, wherein the distal electrode has a surface area ranging between about 1 $mm^2$ and about 8 $mm^2$.

* * * * *